US010662214B2

(12) United States Patent
Ye et al.

(10) Patent No.: US 10,662,214 B2
(45) Date of Patent: May 26, 2020

(54) COMPOUND OF 4'-THIONUCLEOSIDE, AS WELL AS PREPARATION METHOD THEREFOR, PHARMACEUTICAL COMPOSITION THEREOF AND APPLICATION THEREOF

(71) Applicant: Sichuan Kelun-Biotech Biopharmaceutical Co., Ltd., Chengdu, Sichuan (CN)

(72) Inventors: Hong Ye, Sichuan (CN); Gang Liu, Sichuan (CN); Nan Yu, Sichuan (CN); Hong Zeng, Sichuan (CN); Mingliang Zhao, Sichuan (CN); Yan Qing, Sichuan (CN); Hua Deng, Sichuan (CN); Wenjia Li, Sichuan (CN); Donghong Li, Sichuan (CN); Donghai Su, Sichuan (CN); Wei Zhong, Sichuan (CN); Shaohua Li, Sichuan (CN); Xunwei Wu, Sichuan (CN); Lichun Wang, Sichuan (CN); Jingyi Wang, Sichuan (CN)

(73) Assignee: Sichuan Keiun-Biotech Biopharmaceutical Co., Ltd., Sichuan (CN)

( * ) Notice: Subject to any disclaimer, the term of this patent is extended or adjusted under 35 U.S.C. 154(b) by 0 days.

(21) Appl. No.: 15/558,620

(22) PCT Filed: Mar. 28, 2016

(86) PCT No.: PCT/CN2016/077519
§ 371 (c)(1),
(2) Date: Sep. 15, 2017

(87) PCT Pub. No.: WO2016/155593
PCT Pub. Date: Oct. 6, 2016

(65) Prior Publication Data
US 2018/0079770 A1    Mar. 22, 2018

(30) Foreign Application Priority Data

Apr. 3, 2015   (CN) .......................... 2015 1 0157772

(51) Int. Cl.
*A01N 43/04* (2006.01)
*A61K 31/70* (2006.01)
*C07H 19/10* (2006.01)
*C07H 19/20* (2006.01)
*C07H 1/00* (2006.01)
*A61K 31/7068* (2006.01)
*A61K 31/7076* (2006.01)
*A61K 45/06* (2006.01)

(52) U.S. Cl.
CPC ......... *C07H 19/10* (2013.01); *A61K 31/7068* (2013.01); *A61K 31/7076* (2013.01); *A61K 45/06* (2013.01); *C07H 1/00* (2013.01); *C07H 19/20* (2013.01)

(58) Field of Classification Search
None
See application file for complete search history.

(56) References Cited

U.S. PATENT DOCUMENTS

| 5,128,458 A | 7/1992 | Montgomery et al. |
| 6,147,058 A | 11/2000 | Yoshimura et al. |
| 2014/0315850 A1* | 10/2014 | Huang .................. C07H 19/16 514/48 |

FOREIGN PATENT DOCUMENTS

| CN | 107148423 A | 9/2017 |
| EP | 3214090 A1 | 9/2017 |
| JP | 10087687 A2 | 4/1998 |
| WO | 2005012327 A2 | 2/2005 |
| WO | 2005027962 A1 | 3/2005 |
| WO | 2007056596 A2 | 5/2007 |
| WO | 2012045999 A1 | 4/2012 |
| WO | 2014197578 A1 | 12/2014 |
| WO | 2016068341 A1 | 5/2016 |

OTHER PUBLICATIONS

Liu et al. Journal of Fluorine Chemistry (2008), vol. 129, pp. 743-766.*
Brittain "X-Ray Diffraction of Pharmaceutical Materials", Profiles of Drug Substances, Excipients, and Related Methodology (2003), vol. 30, pp. 273-319.*
Youcef Mehellou et al., ["Aryloxy phosphoramidate triesters: a technology for delivering monophosphorylated nucleosides and sugars into cells." ChemMedChem, Nov. 2009, pp. 1779-1791, vol. 4, Issue 11.
Deborah A. Zajchowski et al. "Anti-tumor efficacy of the nucleoside analog 1-(2-deoxy-2-fluoro-4-thio-β-D-arabinofuranosyl) cytosine (4'-thio-FAC) in human pancreatic and ovarian tumor xenograft models." International Journal of Cancer, 2005, pp. 1002-1009, vol. 114, Issue 6.
International Search Report dated Apr. 28, 2016 issued in PCT/CN2016/077519 (4 pages).

(Continued)

*Primary Examiner* — Patrick T Lewis
(74) *Attorney, Agent, or Firm* — Rothwell, Figg, Ernst & Manbeck, P.C.

(57) ABSTRACT

The present invention relates to a novel compound of 4'-thionucleoside, a preparation method therefor, a pharmaceutical composition comprising the same and an application thereof. Specifically, the present invention relates to a phosphamide derivative of 4'-thionucleoside, a preparation method therefor, a pharmaceutical composition comprising the same, a use thereof in the preparation of a medicine for preventing or treating abnormal cell proliferation diseases (for example, tumors or cancers and related diseases) or virus infectious diseases, and a method of using the same for preventing or treating abnormal cell proliferation diseases (for example, tumors or cancers and related diseases) or virus infectious diseases.

18 Claims, 1 Drawing Sheet

(56) References Cited

OTHER PUBLICATIONS

Chinese Office Action issued in Application No. 201680001812.5 dated Sep. 27, 2018, with English machine translation, 21 pages.
The extended European Search Report issued in Application No. 16771348.6 dated Oct. 17, 2018, 13 pages.
Yoshimura, Y. et al., "Synthesis and biological activities of 2'-deoxy-2'-fluoro-4'-thioarabinofuranosyl pyrimidine and -purine nucleosides", Bioorganic & Medical Chemistry, Pergamon, GB, vol. 8, No. 7, Jan. 1, 2000, XP085020195, pp. 1545-1558.
Yoshimura, Y. et al., "An alternative Synthesis of the Antineoplastic Nucleoside 4'-ThioFAC and Its Application to the Synthesis of 4'-ThioFAG and 4'-Thiocytarazid", The Journal of Organic Chemistry, vol. 64, No. 21, Oct. 1, 1999, XP055195175, pp. 7912-7920.
Yoshimura, Y. et al., "A novel synthesis of 2'-modified 2'-deoxy-4'-thiocytidines from D-glucose", The Journal of Organic Chemistry, vol. 62, No. 10, May 16, 1997, XP002606720, pp. 3140-3152.
Pradere, U. et al., "Synthesis of Nucleoside Phosphate and Phosphonate Prodrugs", Chemical Reviews, vol. 114, No. 18, Sep. 24, 2014, XP055203528, pp. 9154-9218.
Slusarczyk, M. et al., "Application of ProTide Technology to Gemcitabine: A Successful Approach to Overcome the Key Cancer Resistance Mechanism Leads to a New Agent (NUC-1031) in Clinical Development", Journal of Medical Chemistry, vol. 57, No. 4, Feb. 27, 2014, XP055205033, pp. 1531-1542.
Tobias, S. et al., "Synthesis and Biological Evaluation of a Cytarabine Phosphoramidate Prodrug", Molecular Pharmaceutics, American Chemical Society, US, vol. 1, No. 2, Mar. 1, 2004, XP009186775, pp. 112-116.
Eurasian Office Action issued in Application No. 201791535/28 dated Apr. 6, 2018, 7 pages.
Second Office Action dated Jul. 5, 2019, for the corresponding Eurasian application No. 201791535 (with English translation), 4 pages.
Examination Report No. 1 for Australian patent application No. 2016240117 dated Oct. 16, 2019, 5 pages.
Notice of Reasons for Rejection issued in the Japanese application No. 2017-541855 dated Nov. 26, 2019, with English translation, 8 pages.

* cited by examiner

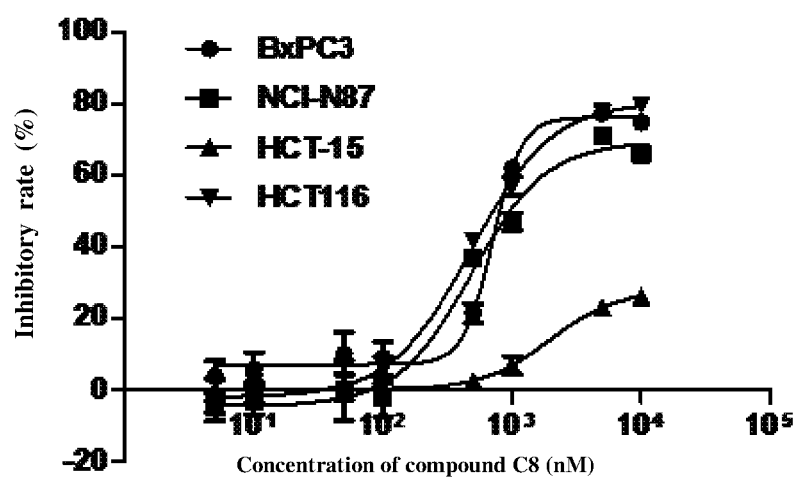

COMPOUND OF 4'-THIONUCLEOSIDE, AS WELL AS PREPARATION METHOD THEREFOR, PHARMACEUTICAL COMPOSITION THEREOF AND APPLICATION THEREOF

CROSS-REFERENCE TO RELATED APPLICATIONS

The present application is a national stage filing under 35 U.S.C. § 371 of PCT/CN2016/077519, filed on 28 Mar. 2016, and claims priority to Chinese patent application 201510157772.0, filed 3 Apr. 2015. Each application is incorporated herein by reference in its entirety.

FIELD OF THE INVENTION

The present invention relates to a novel 4'-thionucleoside compound, to a preparation method thereof, to a pharmaceutical composition comprising the compound, and to use thereof. Specifically, the present invention relates to a phosphamide derivative of a 4'-thionucleoside, to a preparation method thereof, to a pharmaceutical composition comprising the derivative, and to use thereof for the prevention or treatment of an abnormal cell proliferative disease (e.g., tumor, cancer and related disorders) or a viral infectious disease.

BACKGROUND OF THE INVENTION

A natural nucleoside is a glycoside comprising a ribose or a deoxyribose and a base (such as adenine, thymine, guanine, cytosine or uracil), and is an important component of DNA and RNA. Artificially synthesized nucleoside analogues are an important class of chemotherapeutic drugs for tumor, and are referred to as antimetabolites. The effect thereof is mainly achieved by affecting enzymatic system in tumor cells, thereby inhibiting the synthesis of DNA and RNA. According to statistics from WHO, cancer is one of the leading causes of death worldwide. Moreover, drug resistance in cancer cells is ubiquitous, and it is urgently needed to develop new anti-cancer drugs for human health. As such, it is an arduous task in the pharmaceutical industry to develop safe and reliable anti-cancer drugs from various perspectives. Treatment employing an organ specific nucleoside prodrug represents one of the most promising therapeutic methods.

Nucleoside drugs, such as gemcitabine, azacitidine, decitabine, cytarabine, fludarabine, cladribine, 6-azauridine, tiazofurine and atromide, etc., have been widely used for the treatment of various cancers. There are many nucleoside drugs that are currently at different stages of clinical development.

Gemcitabine is a pyrimidine nucleoside analogue developed by Eli Lilly and Company in the US, and is an important nucleoside-based anticancer drug as a first-line therapeutic agent for advanced pancreatic cancer, advanced non-small cell lung cancer, localized or metastatic bladder cancer and metastatic breast cancer. It has a broad spectrum of anti-tumor activity, and is effective for a variety of additional solid tumors. Gemcitabine generally needs to be administered in combination with paclitaxel, cisplatin, and/or carboplatin. Gemcitabine has poor cell permeability, low bioavailability, and a short half-life in cells (between 32~94 min), and thus must be continuously intravenously administered at a high dose (with a recommended dose of 1000 mg/m$^2$), so as to maintain its effective blood drug concentration and toxicity to cancer cells. The dose-limiting toxicity induced by the high dose of gemcitabine employed affects clinical efficacy, and results in a series of side effects and safety issues, such as leukopenia, transaminase abnormalities, proteinuria, as well as nausea and vomiting, etc. In addition, gemcitabine has a number of shortcomings, including lack of tissue specificity which leads to high systemic toxic effects; rapid metabolism and a short plasma half-life; drug resistance in tumors; poor effects achieved through oral administration, common requirement of administration through intravenous injection, a high dosage and severe side effects; poor efficacy achieved when the drug is administered alone, and necessity of co-administration with another anti-cancer drug; etc.

Gemcitabine has poor oral bioavailability, and thus generally needs to be administrated via intravenous injection. The poor oral bioavailability is a result of first-pass metabolism (see Shipley L A., et al., "Metabolism and disposition of gemcitabine, and oncolytic deoxycytidine analog, in mice, rats, and dogs". *Drug Metabolism & Disposition*. 20(6):849-55, 1992). In addition, when dosed orally, gemcitabine is implicated in causing adverse dose-limiting intestinal lesions characterized by moderate-to-marked loss of mucosal epithelium (atrophic enteropathy) throughout the entire length of the intestinal tract in mice given a single oral (gavage) gemcitabine dose of 167, 333, or 500 mg/kg (see Horton N D et al., "Toxicity of single-dose oral gemcitabine in mice", American Association for Cancer Research, Poster Presentation, Orlando, Fla., Mar. 27-31, 2004). In a previous study performed on mice, no death or gastrointestinal toxicity was observed when a significant dose was administered intravenously.

Moreover, gemcitabine, like other nucleoside drugs, is a hydrophilic compound, and thus cannot go through cellular membranes into cells via passive diffusion, but needs a specific transport protein to be delivered into tumor cells. Alteration in the nucleoside transport activity has been considered as an important cause of resistance to gemcitabine. Human equilibrative nucleoside transporter 1 (hENT1) is an important transport protein currently identified for the transportation of gemcitabine into tumor cells. As reduction of intracellular drug accumulation would likely result in decreased sensitivity to gemcitabine, scientists at Clavis Pharma, Norway, have synthesized a 5'-elaidic acid ester derivative of gemcitabine, CP-4126, which has significantly improved lipophilicity than that of gemcitabine. Studies show that CP-4126 can get into tumor cells independent of hENT1 transporter, and thus is expected to exhibit a better anti-tumor effect in tumor patients with a low expression of hENT1.

4'-thionucleoside refers to a nucleoside analogue with the oxygen atom in the furanose ring replaced by a sulfur atom. The synthetic route for 4'-thionucleosides is long and difficult, which greatly limits the study of such compounds. U.S. Pat. No. 6,147,058 discloses a 4'-thionucleoside compound which exhibit inhibitory activity in a colon cancer model in nude mice. This compound is shown to have a better effect in inhibiting tumor growth than that of gemcitabine (Cancer Let. 1999, 144, 177-182; Int. J. Cancer, 2005, 114, 1002-1009). U.S. Pat. No. 5,128,458 discloses a 2',3'-dideoxy-4'-thioribonucleotides with good effects in the treatment of both a viral infectious disease (such as HIV, hepatitis B or C) and an abnormal cell proliferative disease.

Although the 4'-thionucleoside compound has a better effect in inhibiting tumor growth, it also possesses similar shortcomings to those of gemcitabine, such as low oral bioavailability, fast metabolism, multiple adverse effects and drug resistance, etc.

Resistance to 4'-thionucleoside drugs is a main reason for the short survival period of a patient. The major causes for the development of resistance include: 1) lack of corresponding transporter proteins on the surface of tumor cells, which prevents nucleoside drugs from efficiently passing through cellular membranes; 2) low efficiency of the conversion from the drug to the active species as a triphosphate; and 3) metabolism from the drug to an inactive species in the presence of an enzyme.

Since 4'-thionucleoside drug can be quickly metabolized to an inactive species and lose activity, no 4'-thionucleoside drug is available for the treatment of cancers such as liver cancer to date.

So far, problems encountered in the development of 4'-thionucleoside drugs make them difficult to be approved by authorities. A prodrug approach has been employed to overcome such problems. Now a lot of pharmaceutical companies are still working in developing methods for treating cancers by using other prodrugs (see G. Xu, H. L. McLeod, Clin. Cancer Res., 2001, 7, 3314-3324; M. Rooseboom, J. N. M. Commandeur, N. P. E. Vermeulen, Pharmacol. Rev., 2004, 56, 53-102; W. D. Wu, J. Sigmond, G. J. Peters, R. F. Borch, J. Med. Chem. 2007, 50, 3743-3746).

Upon entry into a body, a nucleoside drug would firstly be phosphorylated to form an active metabolite, monophosphate, through the catalysis of a corresponding kinase, and the monophosphate is then converted to a triphosphate. Monophosphorylation of a nucleoside drug is often a rate-limiting step in the metabolism of the drug. Kinases catalyzing the monophosphorylation of a nucleoside in human bodies (thymidine kinase (TK), deoxycytidine kinase (dCK), deoxyguanosine kinase (dGK) and adenosine kinase (AK)) have a limited affinity to nucleosides, and the kinase activity is liable to be inhibited by nucleotide monophosphate (NA-MP). These both limit the in vivo activation of nucleoside drugs, and affect the exhibition of drug activity. To address this issue, researchers have attempted to modify nucleoside drugs through phosphorylation, so as to obtain corresponding phosphates or phosphamide (ChemMedChem, 2009, 4, 1779-1791).

However, in development of a drug through modification, it is difficult to determine whether the modified drug can successfully release the parent drug after entering the body, since the parent drug is different from case to case, and the modified drug often has reduced or no efficacy, or result in new side effects. As such, in years of research, 4'-thionucleoside compounds currently available still have drugability issues, which are difficult to overcome. Today, after gemcitabine is on the market for many years, there is still no 4'-thionucleoside compound approved for clinical application.

SUMMARY OF THE INVENTION

According to an aspect of the present invention, a 4'-thio-2'-fluoronucleoside phosphamide compound as represent by Formula (I) is provided,

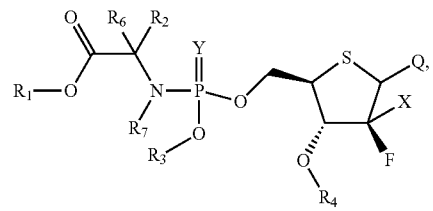

Formula (I)

wherein:

$X$ is hydrogen, $C_{1-6}$ alkyl, halogen, $N_3$, OH, CN or SH;

$Y$ is oxygen or sulfur;

$R_1$, $R_2$, $R_6$, and $R_7$ are each independently selected from the group consisting of hydrogen, optionally substituted $C_{1-10}$ alkyl, optionally substituted cycloalkyl, optionally substituted aryl, optionally substituted heterocyclyl, and optionally substituted heteroaryl, wherein $R_2$ and $R_6$ can be connected to form a 3-8 membered carbocyclic ring which may contain 0-3 heteroatoms selected from N, O, and S, and may be a saturated, unsaturated, or aromatic ring;

$R_3$ is selected from the group consisting of optionally substituted aryl and optionally substituted heteroaryl;

$R_4$ is selected from the group consisting of hydrogen, and optionally substituted $C_{1-10}$ acyl;

$Q$ is a pyrimidine base or a purine base having the following structure:

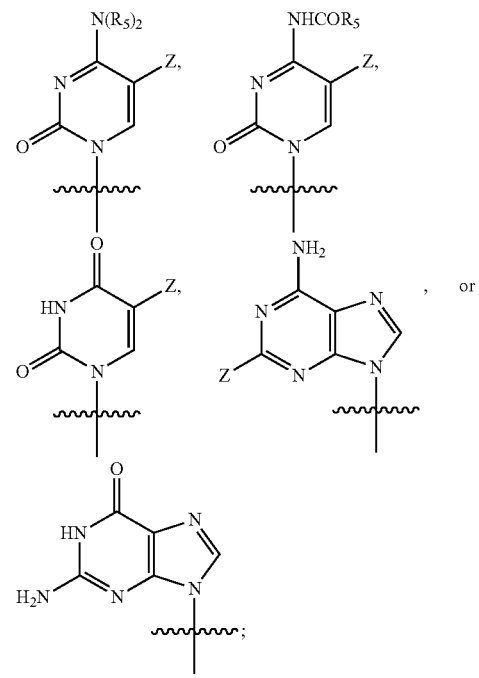

$R_5$ at each occurrence is independently selected from the group consisting of hydrogen, optionally substituted $C_{1-10}$ alkyl and optionally substituted cycloalkyl; and $Z$ is hydrogen, optionally substituted $C_{1-10}$ alkyl or halogen;

the above expression "optionally substituted" means unsubstituted or substituted with one or more substituents independently selected from the group consisting of halogen, alkyl, amino, alkylamino, alkoxy, haloalkyl, haloalkoxy, hydroxy, hydroxyalkyl, alkoxyalkyl, amido, sulfonamido, cyano, nitro, nitroso, azido, aldehyde, alkenyl, alkynyl, cycloalkyl, aryl, aralkyl, aryloxy, heteroaryl, heteroaryloxy, acyl, carboxyl, alkylcarbonyl, arylcarbonyl, heteroarylcarbonyl, and carboxylate; and the substituents can be connected to each other to form a 3-8 membered saturated, unsaturated or aromatic ring containing 0-3 heteroatoms selected from N, O, and S;

or a pharmaceutically acceptable salt, ester, solvate, hydrate, isomer thereof, or any crystalline form or racemate thereof, or a metabolite thereof, or a mixture thereof.

According to another aspect of the present invention, a pharmaceutical composition or a pharmaceutical formulation is provided, wherein the pharmaceutical composition or the pharmaceutical formulation comprises the above 4'-thio-2'-fluoronucleoside phosphamide compound as represent by Formula (I), or a pharmaceutically acceptable salt, ester, hydrate, solvate, isomer thereof, any crystalline form or racemate thereof, a metabolite thereof, or a mixture thereof, as an active ingredient, and a pharmaceutically acceptable carrier, adjuvant, excipient or equivalent pharmaceutically acceptable medium. The pharmaceutical composition or the pharmaceutical formulation can be in a form suitable for administration to a mammal, including a solid preparation, a semi-solid preparation, a liquid preparation, and a gas preparation, etc.

According to a further aspect of the present invention, a use of the above 4'-thio-2'-fluoronucleoside phosphamide compound as represent by Formula (I) in the manufacture of a medicament for the prevention or treatment of an abnormal cell proliferative disease or a viral infectious disease in a mammal is provided. The abnormal cell proliferative disease in a mammal is e.g. cancer and/or tumor and related disorders thereof. Optionally, the medicament further comprises an additional anti-tumour agent.

According to a further aspect of the present invention, a method for the prevention or treatment of an abnormal cell proliferative disease and/or a viral infectious disease in a mammal is provided, wherein the method comprises administering to the mammal an effective amount of the above 4'-thio-2'-fluoronucleoside phosphamide compound as represent by Formula (I), or a pharmaceutically acceptable salt, ester, hydrate, solvate, isomer thereof, any crystalline form or racemate thereof, a metabolite thereof, or a mixture thereof. The abnormal cell proliferative disease in a mammal is e.g. cancer and/or tumor and related disorders thereof in a mammal.

According to a further aspect of the present invention, the above 4'-thio-2'-fluoronucleoside phosphamide compound as represent by Formula (I), or a pharmaceutically acceptable salt, ester, hydrate, solvate, isomer thereof, any crystalline form or racemate thereof, a metabolite thereof, or a mixture thereof for the prevention or treatment of an abnormal cell proliferative disease and/or a viral infectious disease in a mammal is provided. The abnormal cell proliferative disease in a mammal is e.g. cancer and/or tumor and related disorders thereof in a mammal.

According to a further aspect of the present invention, a method for preparing the above compound as represent by Formula (I) is provided, wherein the method comprises the following steps:

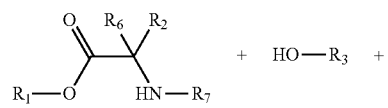

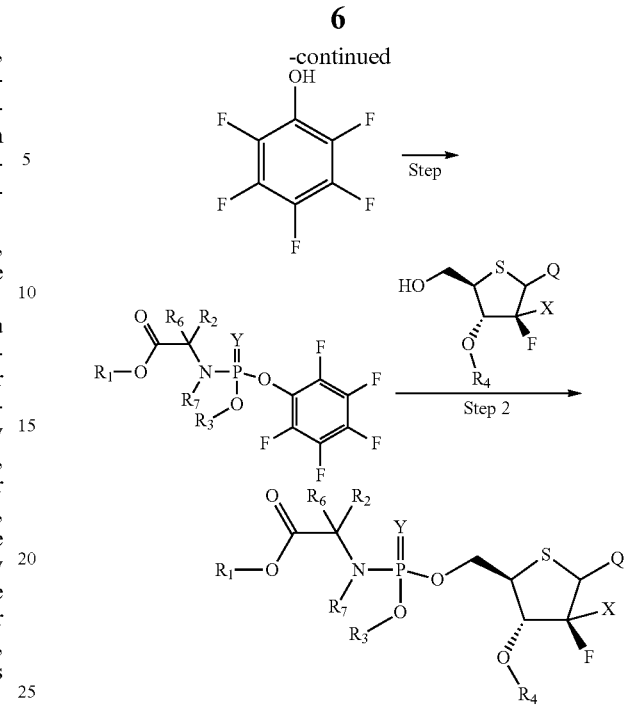

wherein each of the groups is as defined above, and step 1 is preferably performed in the presence of $POCl_3$.

BRIEF DESCRIPTION OF THE DRAWING

The present invention will now be described in more detail with reference to the accompanying drawing, wherein:

FIG. 1 shows the effects of the compound of Example 8 (C8) on four different tumor cells at various concentrations.

DETAILED DESCRIPTION OF THE INVENTION

Compound

An embodiment of the present invention provides a compound of Formula (I), (I)

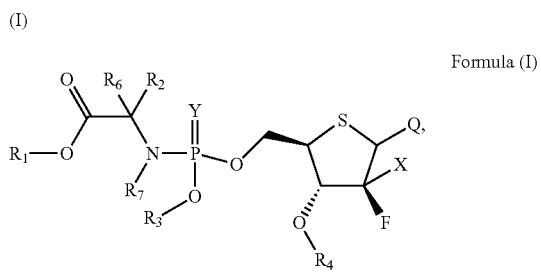

Formula (I)

wherein:

X is hydrogen, $C_{1-6}$ alkyl, halogen, $N_3$, OH, CN or SH;

Y is oxygen or sulfur;

$R_1$, $R_2$, $R_6$, and $R_7$ are each independently selected from the group consisting of hydrogen, optionally substituted $C_{1-10}$ alkyl, optionally substituted cycloalkyl, optionally substituted aryl, optionally substituted heterocyclyl, and optionally substituted heteroaryl, wherein $R_2$ and $R_6$ can be connected to form a 3-8 membered carbocyclic ring which may contain 0-3 heteroatoms selected from N, O, and S, and may be a saturated, unsaturated, or aromatic ring;

$R_3$ is selected from the group consisting of optionally substituted aryl and optionally substituted heteroaryl;

$R_4$ is selected from the group consisting of hydrogen, and optionally substituted $C_{1-10}$ acyl;

Q is a pyrimidine base or a purine base having the following structure:

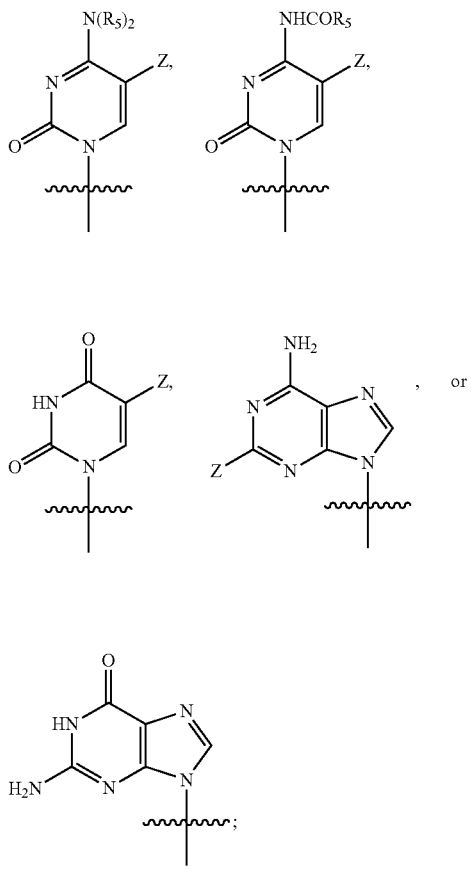

$R_5$ at each occurrence is independently selected from the group consisting of hydrogen, optionally substituted $C_{1-10}$ alkyl and optionally substituted cycloalkyl; and Z is hydrogen, optionally substituted $C_{1-10}$ alkyl or halogen;

the above expression "optionally substituted" means unsubstituted or substituted with one or more substituents selected from the group consisting of halogen, alkyl, amino, alkylamino, alkoxy, haloalkyl, haloalkoxy, hydroxy, hydroxyalkyl, alkoxyalkyl, amido, sulfonamido, cyano, nitro, nitroso, azido, aldehyde, alkenyl, alkynyl, cycloalkyl, aryl, aralkyl, aryloxy, heteroaryl, heteroaryloxy, acyl, carboxyl, alkylcarbonyl, arylcarbonyl, heteroarylcarbonyl, and carboxylate; and the substituents can be connected to each other to form a 3-8 membered saturated, unsaturated or aromatic ring containing 0-3 heteroatoms selected from N, O, and S;

or a pharmaceutically acceptable salt, ester, solvate, hydrate, isomer thereof, or any crystalline form or racemate thereof, or a metabolite thereof, or a mixture thereof.

Another embodiment of the present invention provides the above compound of Formula (I), wherein:

Q is a pyrimidine base having the following structure:

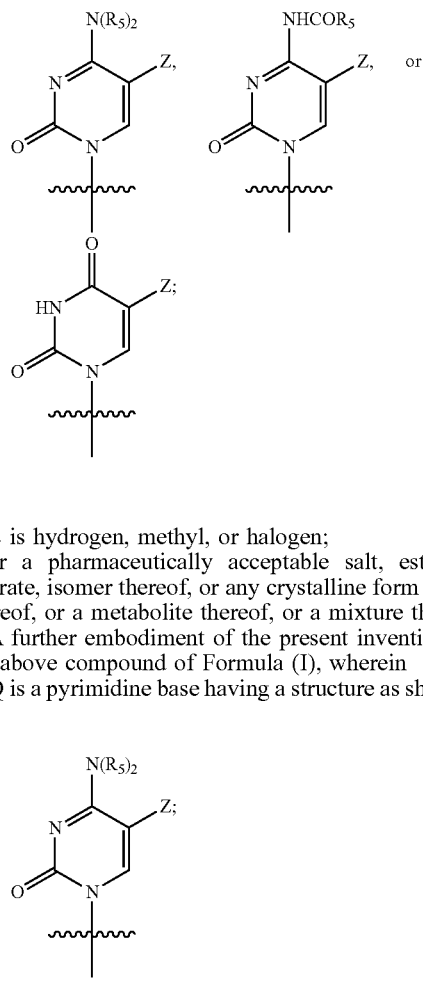

and

Z is hydrogen, methyl, or halogen;

or a pharmaceutically acceptable salt, ester, solvate, hydrate, isomer thereof, or any crystalline form or racemate thereof, or a metabolite thereof, or a mixture thereof.

A further embodiment of the present invention provides the above compound of Formula (I), wherein Q is a pyrimidine base having a structure as shown below:

$$\text{(structure)}$$

and

Z is hydrogen, methyl, or halogen;

or a pharmaceutically acceptable salt, ester, solvate, hydrate, isomer thereof, or any crystalline form or racemate thereof, or a metabolite thereof, or a mixture thereof.

A further embodiment of the present invention provides the above compound of Formula (I), wherein:

$R_1$, $R_2$, $R_6$, and $R_7$ are each independently selected from the group consisting of hydrogen, optionally substituted $C_{1-10}$ alkyl, optionally substituted cycloalkyl, and optionally substituted aryl, wherein $R_2$ and $R_6$ can be connected to form a 3-8 membered carbocyclic ring which may contain 0-3 heteroatoms selected from N, O, and S, and may be a saturated, unsaturated, or aromatic ring;

Q is cytosine having the following structural formula:

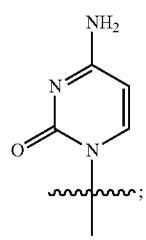 [SMILES: *n1ccc(N)nc1=O]

or a pharmaceutically acceptable salt, ester, solvate, hydrate, isomer thereof, or any crystalline form or racemate thereof, or a metabolite thereof, or a mixture thereof.

A further embodiment of the present invention provides the above compound of Formula (I), wherein Q is selected from

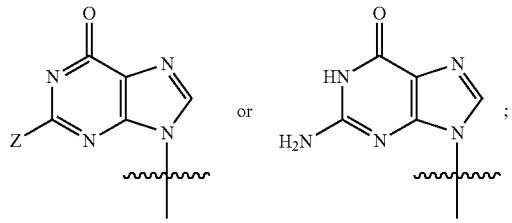

or a pharmaceutically acceptable salt, ester, solvate, hydrate, isomer thereof, or any crystalline form or racemate thereof, or a metabolite thereof, or a mixture thereof.

A further embodiment of the present invention provides the above compound of Formula (I), wherein X is hydrogen or halogen, and the halogen is fluorine, chlorine, bromine or iodine.

A further embodiment of the present invention provides the above compound of Formula (I), wherein Y is oxygen.

A further embodiment of the present invention provides the above compound of Formula (I), wherein $R_1$, $R_2$, $R_6$, and $R_7$ are each independently selected from the group consisting of hydrogen, optionally substituted $C_{1-10}$ alkyl, and optionally substituted aryl (preferably optionally substituted $C_{6-14}$ aryl), the above expression "optionally substituted" means unsubstituted or substituted with one or more substituents selected from the group consisting of halogen, $C_{1-6}$ alkyl, and $C_{6-14}$ aryl. Most preferably, $R_1$, $R_2$, $R_6$, and $R_7$ are each independently selected from the group consisting of hydrogen, methyl, ethyl, propyl, isopropyl, phenyl, benzyl, and 4-fluorobenzyl.

A further embodiment of the present invention provides the above compound of Formula (I), wherein $R_3$ is selected from the group consisting of optionally substituted aryl, preferably optionally substituted $C_{6-14}$ aryl, more preferably optionally substituted phenyl, the above expression "optionally substituted" means unsubstituted or substituted with one or more substituents selected from the group consisting of halogen, $C_{1-6}$ alkyl, and $C_{1-6}$ alkoxy, and the substituents can be connected to each other to form a 3-8 membered saturated, unsaturated or aromatic ring containing 0-3 (e.g. 1, 2, or 3) O. Most preferably, $R_3$ has a structure as shown below:

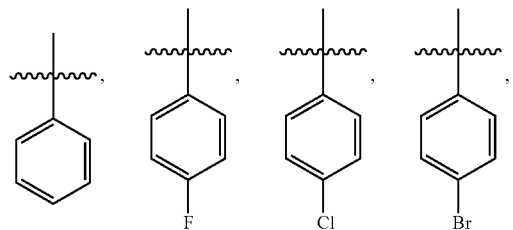

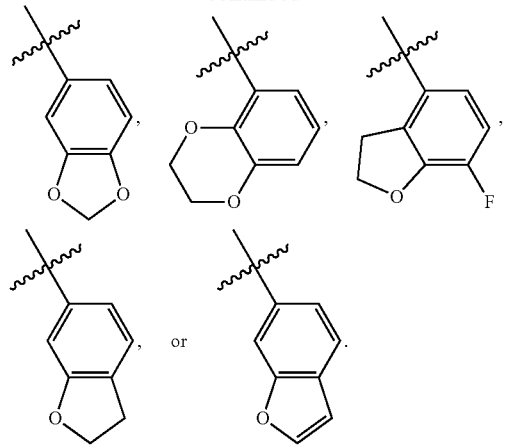

A further embodiment of the present invention provides the above compound of Formula (I), wherein $R_4$ is hydrogen.

A further embodiment of the present invention provides the above compound of Formula (I), wherein $R_5$ at each occurrence is independently selected from the group consisting of hydrogen and optionally substituted $C_{1-10}$ alkyl (e.g. hept-4-yl).

A further embodiment of the present invention provides the above compound of Formula (I), wherein Z is hydrogen, methyl, fluorine or chlorine.

The present invention encompasses the above compound of Formula (I) obtained by any combination of groups in the definitions of the above-described various embodiments, and would not be constrained by each individual embodiment.

A further embodiment of the present invention provides the above compound of Formula (I), wherein Q is

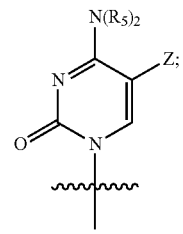

X is hydrogen, $C_{1-6}$ alkyl, halogen, $N_3$, OH, CN or SH;

Y is oxygen or sulfur;

$R_1$, $R_2$, $R_6$, and $R_7$ are each independently selected from the group consisting of hydrogen, optionally substituted $C_{1-10}$ alkyl, optionally substituted cycloalkyl, optionally substituted aryl, optionally substituted heterocyclyl, and optionally substituted heteroaryl, wherein $R_2$ and $R_6$ can be connected to form a 3-8 membered carbocyclic ring which may contain 0-3 heteroatoms selected from N, O, and S, and may be a saturated, unsaturated, or aromatic ring;

$R_3$ is selected from the group consisting of optionally substituted aryl and optionally substituted heteroaryl;

$R_4$ is selected from the group consisting of hydrogen, and optionally substituted $C_{1-10}$ acyl;

$R_5$ at each occurrence is independently selected from the group consisting of hydrogen, optionally substituted $C_{1-10}$ alkyl and optionally substituted cycloalkyl; and Z is hydrogen, methyl or halogen;

the above expression "optionally substituted" means unsubstituted or substituted with one or more substituents selected from the group consisting of halogen, alkyl, amino, alkylamino, alkoxy, haloalkyl, haloalkoxy, hydroxy, hydroxyalkyl, alkoxyalkyl, amido, sulfonamido, cyano, nitro, nitroso, azido, aldehyde, alkenyl, alkynyl, cycloalkyl, aryl, aralkyl, aryloxy, heteroaryl, heteroaryloxy, acyl, carboxyl, alkylcarbonyl, arylcarbonyl, heteroarylcarbonyl, and carboxylate; and the substituents can be independent from each other, or be connected to each other to form a 3-8 membered saturated, unsaturated or aromatic ring containing 0-3 heteroatoms selected from N, O, and S;

or a pharmaceutically acceptable salt, ester, solvate, hydrate, isomer thereof, or any crystalline form or racemate thereof, or a metabolite thereof, or a mixture thereof.

A further embodiment of the present invention provides the above compound of Formula (I), wherein Q is cytosine having the following structural formula:

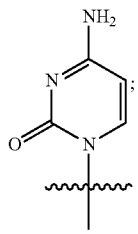 [SMILES: *n1ccc(N)nc1=O]

X is hydrogen, $C_{1-6}$ alkyl, halogen, $N_3$, OH, CN or SH;

Y is oxygen or sulfur;

$R_1$, $R_2$, $R_6$, and $R_7$ are each independently selected from the group consisting of hydrogen, optionally substituted $C_{1-10}$ alkyl, optionally substituted cycloalkyl, and optionally substituted aryl, wherein $R_2$ and $R_6$ can be connected to form a 3-8 membered carbocyclic ring which may contain 0-3 heteroatoms selected from N, O, and S, and may be a saturated, unsaturated, or aromatic ring;

$R_3$ is selected from the group consisting of optionally substituted aryl and optionally substituted heteroaryl;

$R_4$ is selected from the group consisting of hydrogen, and optionally substituted $C_{1-10}$ acyl;

$R_5$ at each occurrence is independently selected from the group consisting of hydrogen, optionally substituted $C_{1-10}$ alkyl and optionally substituted cycloalkyl; and Z is hydrogen, optionally substituted $C_{1-10}$ alkyl or halogen;

the above expression "optionally substituted" means unsubstituted or substituted with one or more substituents selected from the group consisting of halogen, alkyl, amino, alkylamino, alkoxy, haloalkyl, haloalkoxy, hydroxy, hydroxyalkyl, alkoxyalkyl, amido, sulfonamido, cyano, nitro, nitroso, azido, aldehyde, alkenyl, alkynyl, cycloalkyl, aryl, aralkyl, aryloxy, heteroaryl, heteroaryloxy, acyl, carboxyl, alkylcarbonyl, arylcarbonyl, heteroarylcarbonyl, and carboxylate; and the substituents can be connected to each other to form a 3-8 membered saturated, unsaturated or aromatic ring containing 0-3 heteroatoms selected from N, O, and S;

or a pharmaceutically acceptable salt, ester, solvate, hydrate, isomer thereof, or any crystalline form or racemate thereof, or a metabolite thereof, or a mixture thereof.

A further embodiment of the present invention provides the above compound of Formula (I),

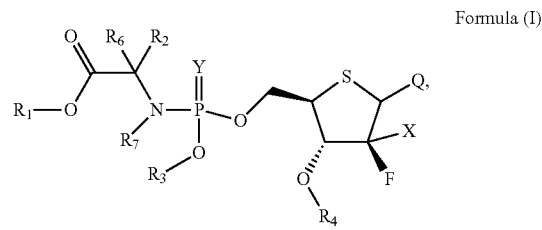

wherein:

X is hydrogen, $C_{1-6}$ alkyl, halogen, $N_3$, OH, CN or SH;

Y is oxygen or sulfur;

$R_1$, $R_2$, $R_6$, and $R_7$ are each independently selected from the group consisting of hydrogen, optionally substituted $C_{1-10}$ alkyl, optionally substituted cycloalkyl, and optionally substituted aryl, wherein $R_2$ and $R_6$ can be connected to form a 3-8 membered carbocyclic ring which may contain 0-3 heteroatoms selected from N, O, and S, and may be a saturated, unsaturated, or aromatic ring;

$R_3$ is selected from the group consisting of optionally substituted aryl and optionally substituted heteroaryl;

$R_4$ is selected from the group consisting of hydrogen, and optionally substituted $C_{1-10}$ acyl;

Q is a purine base having the following structure:

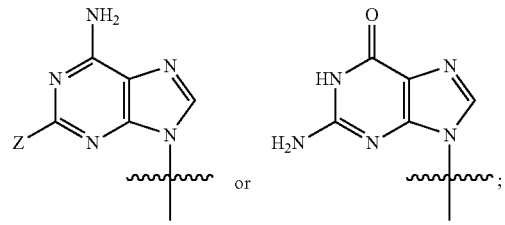

$R_5$ at each occurrence is independently selected from the group consisting of hydrogen, optionally substituted $C_{1-10}$ alkyl and optionally substituted cycloalkyl; and Z is hydrogen, methyl or halogen;

the above expression "optionally substituted" means unsubstituted or substituted with one or more substituents selected from the group consisting of halogen, alkyl, amino, alkylamino, alkoxy, haloalkyl, haloalkoxy, hydroxy, hydroxyalkyl, alkoxyalkyl, amido, sulfonamido, cyano, nitro, nitroso, azido, aldehyde, alkynyl, alkenyl, cycloalkyl, aryl, aralkyl, aryloxy, heteroaryl, heteroaryloxy, acyl, carboxyl, alkylcarbonyl, arylcarbonyl, heteroarylcarbonyl, and carboxylate; and the substituents can be independent from each other, or be connected to each other to form a 3-8 membered saturated, unsaturated or aromatic ring containing 0-3 heteroatoms selected from N, O, and S;

or a pharmaceutically acceptable salt, ester, solvate, hydrate, isomer thereof, or any crystalline form or racemate thereof, or a metabolite thereof, or a mixture thereof.

A further embodiment of the present invention provides the above compound of Formula (I), which is a 4'-thio-2,2-difluoronucleoside phosphamide compound (i.e., X in Formula (I) is F), and Q is a pyrimidine group in its definition, and the remaining substituents are each as defined as above.

A further embodiment of the present invention provides the above compound of Formula (I), which is a 4'-thio-2,2- difluoronucleoside phosphamide compound (i.e., X in Formula (I) is F), and Q is a cytosine group in its definition, and the remaining substituents are each as defined as above.
The preferred compounds of the present invention are as follows:
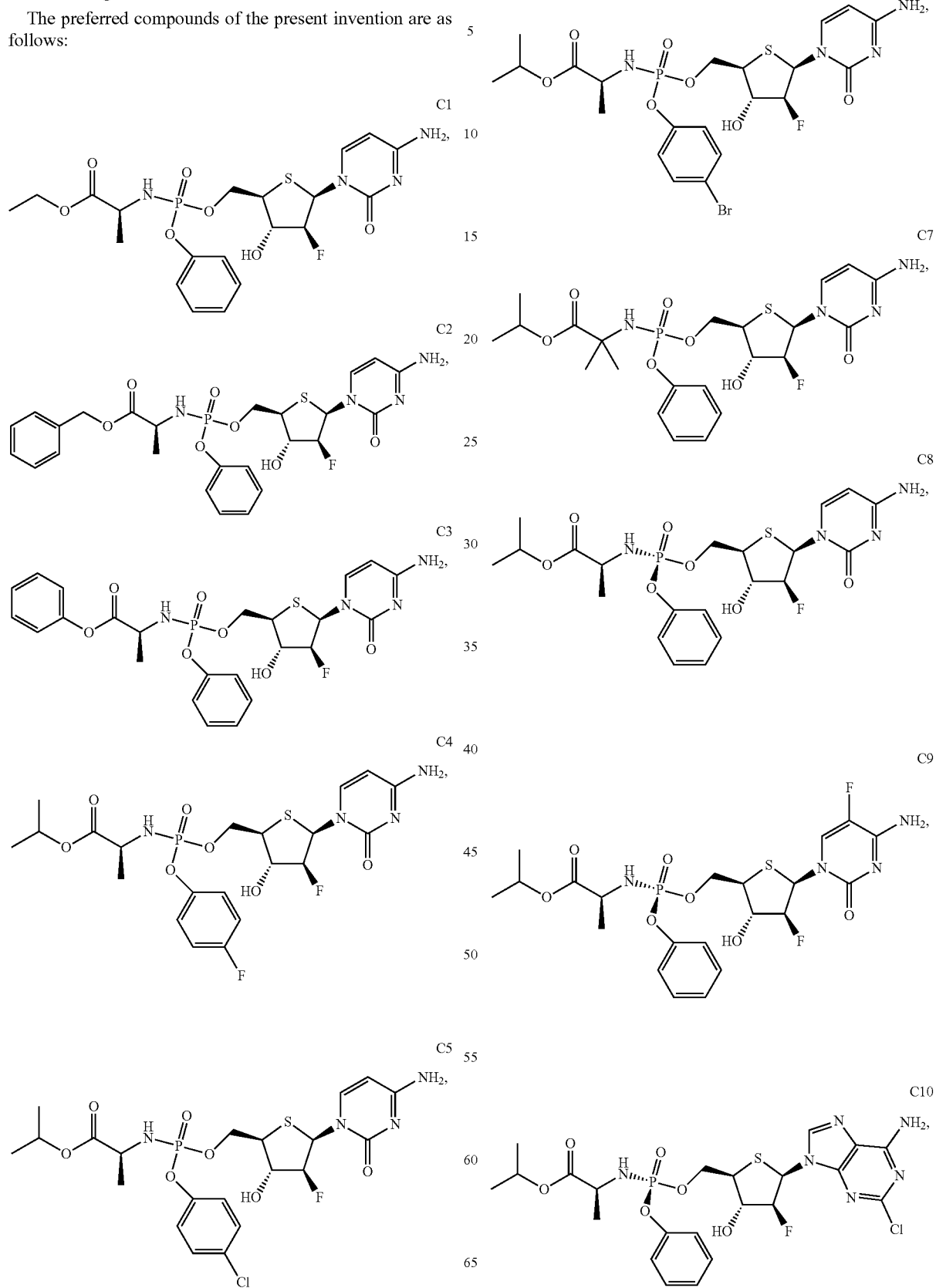

-continued

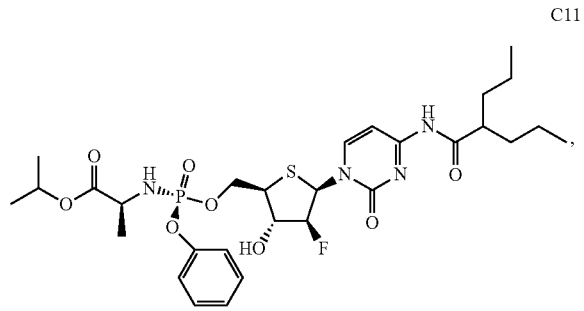
C11

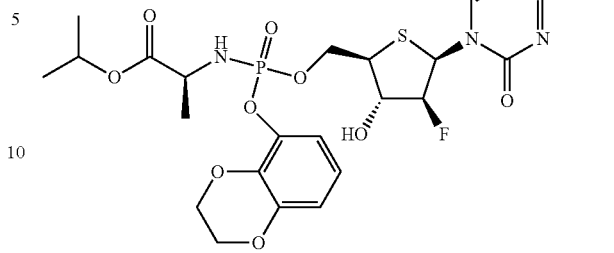
C16

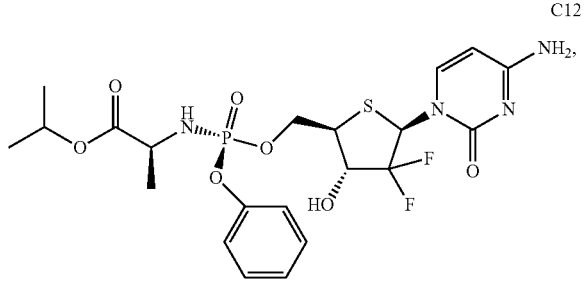
C12

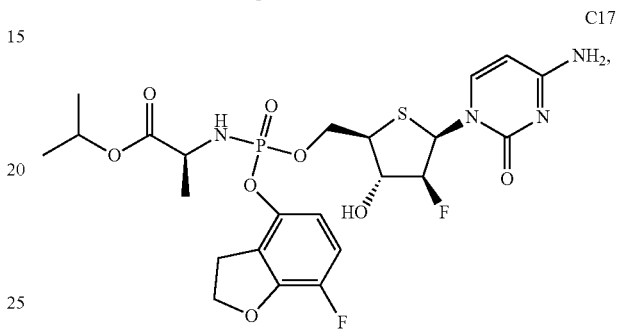
C17

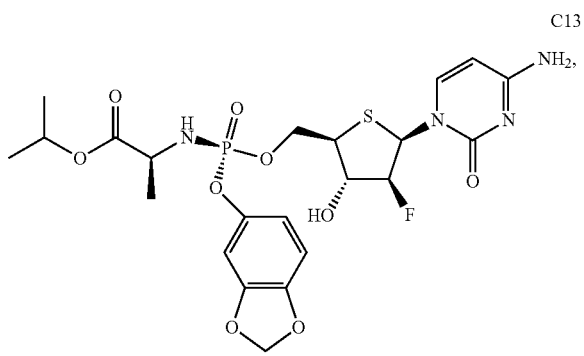
C13

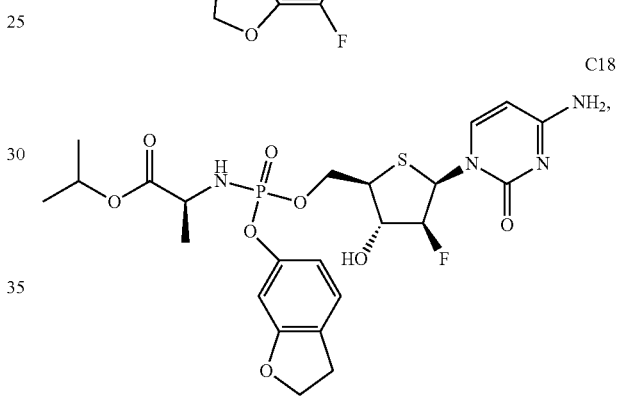
C18

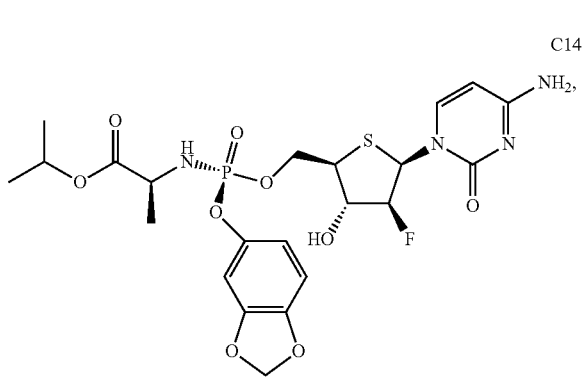
C14 or

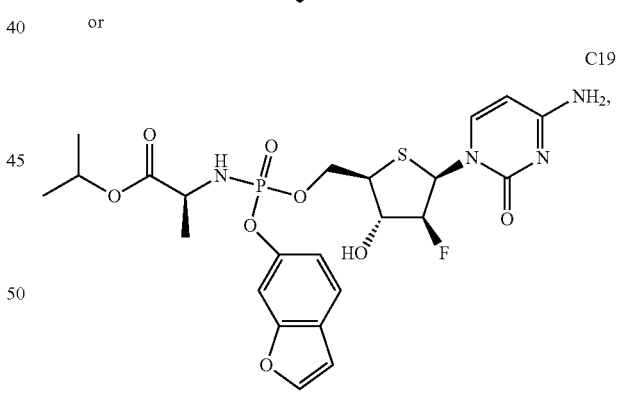
C19

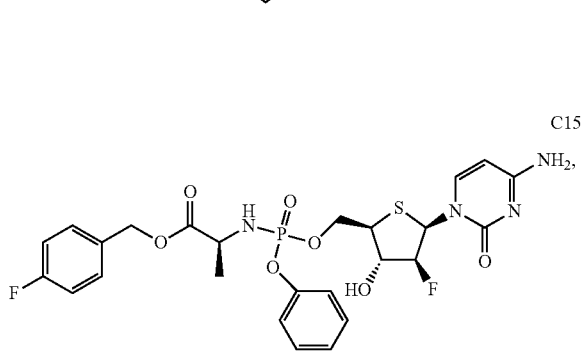
C15 or a pharmaceutically acceptable salt, ester, solvate, hydrate, isomer thereof, or any crystalline form or racemate thereof, or a metabolite thereof, or a mixture thereof.

In extensive research, structural modifications and activity screening are made to the 4'-thio-2'-fluoronucleoside compound in the present application, and the compound with a specific phosphamide substituent at position 5 of the present invention is obtained. The compound of the present invention has superior pharmaceutical efficacy, including an anti-tumor/anti-cancer effect and an effect on a viral infectious disease, as well as increased liposolubility, improved bioavailability, reduced irritation, and improved absorption.

Issues in metabolic rate present in existing drugs are addressed, toxicity is significantly reduced, and safety profile is improved. The pharmacological effect can be achieved through various administration routes.

The compound of Formula (I) described in the present invention refers to all the compounds covered by Formula (I), pharmaceutically acceptable salts, esters, hydrates, solvates, isomers thereof, or any crystalline form or racemate thereof, or metabolites thereof, or mixtures thereof.

A further embodiment of the present invention provides a pharmaceutical composition, comprising the compound of Formula (I), or a pharmaceutically acceptable salt, ester, hydrate, solvate, isomer thereof, or any crystalline form or racemate thereof, or a metabolite thereof, or a mixture thereof, as an active ingredient, and a pharmaceutically acceptable carrier, adjuvant, excipient or equivalent pharmaceutically acceptable medium.

The pharmaceutical composition may comprise the compound of Formula (I) in a unit dose ranging from 0.1-1000 mg, preferably 1-800 mg, more preferably 10-600 mg, particularly preferably 50-450 mg, and most preferably 100-300 mg.

The pharmaceutical composition may be in a form of e.g., a solid, semi-solid, liquid, or gas preparation. In particular, the solid preparation is e.g. a tablet, capsule, powder, granule, or suppository, etc.; the liquid preparation is e.g. a solution, suspension or injection. The composition can also be a preparation such as liposome, and microsphere. Particularly, the pharmaceutical composition is in a dosage form suitable for oral administration.

The pharmaceutical composition can be in a form of a single dose unit or multiple dose units, each of the dose unit comprises a suitable amount of the compound of Formula (I), or a pharmaceutically acceptable salt, ester, hydrate, solvate, isomer thereof, or any crystalline form or racemate thereof, or a metabolite thereof, or a mixture thereof.

A further embodiment of the present invention provides a use of the compound of Formula (I), or a pharmaceutically acceptable salt, ester, hydrate, solvate, isomer thereof, any crystalline form or racemate thereof, a metabolite thereof, or a mixture thereof as an active ingredient in the manufacture of a medicament for the prevention or treatment of an abnormal cell proliferative disease or a viral infectious disease in a mammal. The medicament may comprise the compound of Formula (I) in a unit dose ranging from 0.1-1000 mg, preferably 1-800 mg, more preferably 10-600 mg, particularly preferably 50-450 mg, and most preferably 100-300 mg.

A further embodiment of the present invention provides a method for the treatment or prevention of an abnormal cell proliferative disease or a viral infectious disease in a mammal, wherein the method comprises administering to the mammal an effective amount of the compound of Formula (I), or a pharmaceutically acceptable salt, ester, hydrate, solvate, isomer thereof, any crystalline form or racemate thereof, a metabolite thereof, or a mixture thereof.

A further embodiment of the present invention provides the compound of Formula (I), or a pharmaceutically acceptable salt, ester, hydrate, solvate, isomer thereof, any crystalline form or racemate thereof, a metabolite thereof, or a mixture thereof for the treatment or prevention of an abnormal cell proliferative disease or a viral infectious disease in a mammal.

The abnormal cell proliferative disease or the viral infectious disease is e.g. cancer and/or tumor and related disorders thereof. The cancer and/or tumor include(s) tumors and/or cancers and related disorders in esophagus, stomach, intestine, rectum, mouth, pharynx, larynx, lung, colon, breast, uterus, endometrium, ovary, prostate, testis, bladder, kidney, liver, pancreas, bone, connective tissue, skin, eye, brain and central nervous system, as well as thyroid cancer, leukemia, Hodgkin disease, lymphoma and myeloma.

The compound of Formula (I), or a pharmaceutically acceptable salt, ester, hydrate, solvate, isomer thereof, any crystalline form or racemate thereof, a metabolite thereof, or a mixture thereof can be administered in combination with an additional anti-tumour agent for the prevention or treatment of an abnormal cell proliferative disease (such as cancer and/or tumor and related disorders thereof) in a mammal. The additional anti-tumor agent refers to a substance with activity against tumor/cancer and related disorders thereof, and includes but is not limited to erlotinib or cisplatin.

The compound of Formula (I), or a pharmaceutically acceptable salt, ester, hydrate, solvate, isomer thereof, any crystalline form or racemate thereof, a metabolite thereof, or a mixture thereof can be administered in combination with an additional anti-viral agent for the prevention or treatment of a viral infectious disease. The additional anti-viral agent includes but is not limited to lamivudine, entecavir, nevirapine or stavudine.

The expression "administered in combination" encompasses two or more drugs are administered simultaneously, sequentially, or alternatively, and particularly encompasses two or more drugs are prepared into one or more dose units, so as to obtain a pharmaceutical product suitable for administration in combination, which is administered to a mammal in need thereof.

A further embodiment of the present invention provides a method for preparing the compound of Formula (I), comprising the following steps:

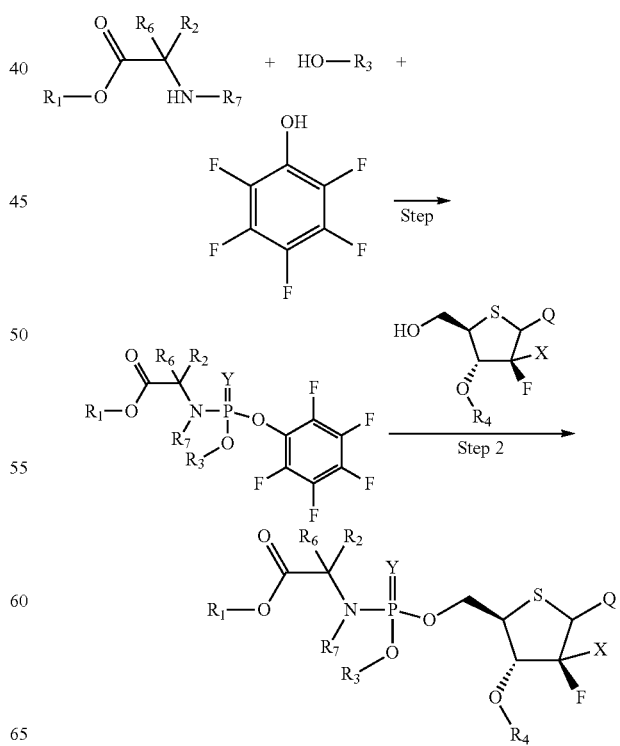

wherein each of the groups is as defined above, and step 1 is preferably performed in the presence of $POCl_3$.

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that most of the following terms will be readily understood by a person skilled in the art, the following definitions are nevertheless put forth to better illustrate the present invention.

The expression "as defined above" refers to the first and/or the broadest definition provided in the application, as well as scenarios suitable in the context.

The terms "contain", "include", "comprise", "have", or "relate to", as well as other variations used herein are inclusive or open-ended, and do not exclude additional, unrecited elements or method steps.

As used herein, the term "compound of the present invention" generally refers to the scope of compounds defined by above Formula (I), or pharmaceutically acceptable salts, esters, hydrates, solvates, isomers thereof, any crystalline form or racemate thereof, metabolites thereof, or mixtures thereof.

As used herein, the term "metabolite" refers to a compound generated in vivo after a drug is applied to a subject in need thereof.

As used herein, the term "pharmaceutically acceptable salt" refers to those salts which retain the biological effectiveness and properties of the parent compound, and can be prepared in the following manner: a proton-accepting moiety is partially protonated and/or a proton-donating moiety is partially deprotonated. It should be noted that the partial protonation of the proton-accepting moiety results in a cationic species, the charge of which is balanced by the presence of a physiological anion, while the partial deprotonation of the proton-donating moiety results in an anionic species, the charge of which is balanced by the presence of a physiological cation.

A pharmaceutically acceptable salt of the compound of Formula (I) includes an acid addition salt and a base addition salt thereof.

A suitable acid addition salt is formed from an acid which forms a non-toxic salt and includes an inorganic acid and an organic acid. In the present invention, a suitable inorganic acid is an acid as defined in the field of chemistry, such as hydrochloric acid, sulfuric acid or phosphoric acid, etc. A suitable organic acid includes an organic sulfonic acid, an organic carboxylic acid, or an amino acid, etc. A suitable organic sulfonic acid is e.g. $C_{6-16}$ aryl sulfonic acid, $C_{6-16}$ heteroaryl sulfonic acid, or $C_{1-16}$ alkyl sulfonic acid, and a suitable organic carboxylic acid is e.g. monocarboxylic acid or polycarboxylic acid, including $C_{1-16}$ alkyl carboxylic acid, $C_{6-16}$ aryl carboxylic acid and $C_{4-16}$ heteroaryl carboxylic acid. The organic carboxylic acid can also be e.g. an amino acid, various kinds of which are suitable, particularly natural amino acids which are found as components of proteins. Specific examples of salts formed from the above acids include the acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

A suitable base addition salt is formed from a base which forms non-toxic salts and includes an inorganic base and an organic base. Specific examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, 2002). Methods for preparing pharmaceutically acceptable salts of compounds of the present invention are known to a person skilled in the art.

As used herein, the term "isomer" refers to a different compound with a same molecular formula, and includes a stereoisomer. The term "stereoisomer" is an isomer that merely differs in the arrangement of atoms in space. α- and β-indicate the specific stereochemical configuration of a substituent at an asymmetric carbon atom in a chemical structure as drawn.

The compound of the present invention may have one or more chiral centers, and may, therefore, exist in a variety of stereoisomeric configurations. Due to the presence of these chiral centers, the compound of the present invention can exist as a racemate, a mixture of enantiomers, as well as mixtures of each enantiomer and a diastereomer and of diastereomers. All such racemates, enantiomers, and diastereomers are within the scope of "the compound of the present invention". The terms "R" and "S" are used in organic chemistry to denote specific configurations of a chiral center.

The compound of the present invention can exist as a hydrate, or as a solvate, wherein the compound of the present invention contains a polar solvent, in particular water, methanol or ethanol for example as a structural element of the crystal lattice of the compound. The amount of the polar solvent, in particular water, may exist in a stoichiometric or non-stoichiometric ratio.

The present invention includes all possible crystalline forms, or polymorphs, of the compound of the present invention, either as a single polymorph, or as a mixture of more than one polymorphs, in any ratio.

The term "optional" or "optionally" means an element may be, but is not necessarily, present in a corresponding situation or condition. The term comprises an example wherein a substituent is or is not present, and also comprises an example which is substituted with one or more substituents. The term "substituted" means that one or more (e.g., one, two, three, or four) hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. In the compound of Formula (I) of the present invention, the expression "optionally substituted" covers situations where a compound is substituted with one or more substituents, and when the expression "optionally substituted" refers to a situation where a compound is substituted with multiple substituents, the substituents may be appropriately connected to each other to form a saturated, unsaturated or aromatic ring containing 0-3 heteroatoms selected from oxygen (O), nitrogen (N), and sulfur (S), and such saturated, unsaturated or aromatic ring may further form a ring with the group being substituted. For example, specific examples of the term "optionally substituted aryl" include dihydrobenzothiophenyl, as well as a group having the follow structure:

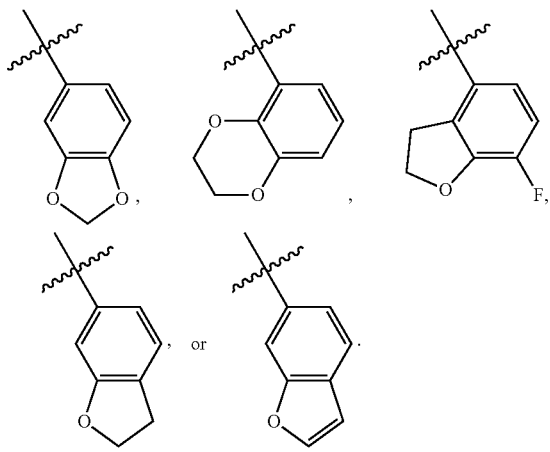

As used herein, the term "alkyl" refers to an unbranched or branched, chain or cyclic, saturated, monovalent hydrocarbon residue, which preferably contains 1 to 14 carbon atoms ($C_{1-14}$ alkyl), more preferably contains 1 to 10 carbon atoms ($C_{1-10}$ alkyl), more preferably contains 1 to 6 carbon atoms ($C_{1-6}$ alkyl), and particularly preferably contains 1 to 4 carbon atoms ($C_{1-4}$ alkyl). Examples of an alkyl group include, but are not limited to, lower alkyl groups including methyl, ethyl, propyl, isopropyl, n-butyl, isobutyl, tert-butyl or pentyl, isopentyl, neopentyl, hexyl, heptyl (e.g., hept-4-yl) and octyl.

As used herein, the term "cycloalkyl" refers to a saturated, non-aromatic, monocyclic or polycyclic (such as bicyclic) hydrocarbon ring. When a cycloalkyl comprises two or more rings, the rings can be fused together. In its ring, a cycloalkyl group may contain 3 to 10 atoms ($C_{3-10}$ cycloalkyl), preferably 3 to 8 ring atoms ($C_{3-8}$ cycloalkyl), more preferably 3 to 6 ring atoms ($C_{3-6}$ cycloalkyl), and particularly preferably 3 to 4 ring atoms ($C_{3-4}$ cycloalkyl). The cycloalkyl group includes, but is not limited to monocycles such as cyclopropyl, cyclobutyl, cyclopentyl, cyclohexyl, cycloheptyl, cyclooctyl, cyclononyl, or bicycicles, including spiro, fused, or bridged systems (such as bicyclo[1.1.1]pentanyl, bicyclo[2.2.1]heptanyl, bicyclo[3.2.1]octanyl or bicyclo[5.2.0]nonanyl, decahydronaphthalenyl, etc.), optionally substituted with 1 or more (such as 1 to 3) suitable substituents.

Unless otherwise indicated, the term "alkenyl" as used herein refers to a hydrocarbon residue having 2 to 10 carbon atoms and having one or two olefinic double bonds, and it preferably contains 2-8 carbon atoms ($C_{2-8}$ alkenyl), more preferably contains 2 to 6 carbon atoms ($C_{2-6}$ alkenyl), and particularly preferably contains 2 to 4 carbon atoms ($C_{2-4}$ alkenyl). Examples of an alkenyl group include vinyl, 1-propenyl, 2-propenyl or 2-butenyl, etc.

Unless otherwise indicated, the term "alkynyl" as used herein refers to an unbranched or branched hydrocarbon chain group having 2 to 10 carbon atoms ($C_{2-10}$ alkynyl), and having one or two triple bonds, and it preferably contains 2-8 carbon atoms ($C_{2-8}$ alkynyl), more preferably contains 2 to 6 carbon atoms ($C_{2-6}$ alkynyl), and particularly preferably contains 2 to 4 carbon atoms ($C_{2-4}$ alkynyl).

Examples of an alkynyl group are ethynyl, 1-propynyl, 2-propynyl, 1-butynyl, 2-butynyl or 3-butynyl.

As used herein, the term "amino" represents $—NH_2$, and alkylamino represents $—NR'R''$, wherein R' and R" are the same or different, and are H or an alkyl or cycloalkyl group as defined above.

As used herein, the term "alkoxy" represents —O-alkyl, wherein alkyl is as defined above (e.g., $C_{1-14}$ alkyl, $C_{1-10}$ alkyl, $C_{1-6}$ alkyl, or $C_{1-4}$ alkyl), such as methoxy, ethoxy, n-propoxy, isopropoxy, n-butoxy, isobutoxy, tert-butoxy, pentoxy, hexoxy, etc., as well as isomers thereof.

As used herein, the term "halogen" or "halo" refers to fluorine, chlorine, bromine or iodine.

As used herein, the term "haloalkyl" refers to the alkyl group as defined above, wherein 1, 2, 3, or more hydrogen atoms are replaced with halogens. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

As used herein, the term "haloalkoxy" refers to the alkoxy group as defined above, wherein 1, 2, 3, or more hydrogen atoms are replaced with halogens.

As used herein, the term "acyl" represents a group of formula $—C(=O)R$, wherein R is hydrogen or an alkyl group as defined above (e.g., $C_{1-14}$ alkyl, $C_{1-10}$ alkyl, $C_{1-6}$ alkyl, or $C_{1-4}$ alkyl).

As used herein, the term "alkylcarbonyl" represents a group of formula $—C(=O)R$, wherein R is an alkyl group as defined above (e.g., $C_{1-14}$ alkyl, $C_{1-10}$ alkyl, $C_{1-6}$ alkyl, or $C_{1-4}$ alkyl).

As used herein, the term "amido" represents a group of formula $—NC(=O)R'R''$, wherein R and R" are the same or different, and are hydrogen or an alkyl group as defined above (e.g., $C_{1-14}$ alkyl, $C_{1-10}$ alkyl, $C_{1-6}$ alkyl, or $C_{1-4}$ alkyl).

As used herein, the term "hydroxyalkyl" represents a group of formula $—R—OH$, wherein R is an alkylene group. Unless otherwise indicated, the term "alkylene" as used herein refers to a divalent, saturated, straight hydrocarbon group containing 1 to 10 carbon atoms ($C_{1-10}$ alkylene), more preferably 1 to 6 carbon atoms ($C_{1-6}$ alkylene), and particularly preferably 1 to 4 carbon atoms ($C_{1-4}$ alkylene), or a branched, saturated, divalent hydrocarbon group containing 3-10 carbon atoms ($C_{3-10}$ alkylene), more preferably 3-8 carbon atoms ($C_{3-8}$ alkylene), and particularly preferably 3-5 carbon atoms ($C_{3-5}$ alkylene). Examples of an alkylene group include, but are not limited to, methylene, ethylene, propylene, 2-methyl-propylene, butylene and 2-ethylbutylene, etc.

As used herein, the term "aryl" refers to a group having at least one aromatic ring, i.e., having a conjugated π-electron system, and includes a monocyclic aryl group, and a bicyclic aryl group. It contains 6-14 carbon atoms ($C_{6-14}$ aryl), such as phenyl and naphthyl, etc. Optionally substituted aryl includes an aryl group substituted with multiple substituents, and the substituents can be appropriately connected to each other to form a saturated, unsaturated or aromatic ring containing 0-3 heteroatoms selected from N, O, and S. The aryl group preferably includes the following groups:

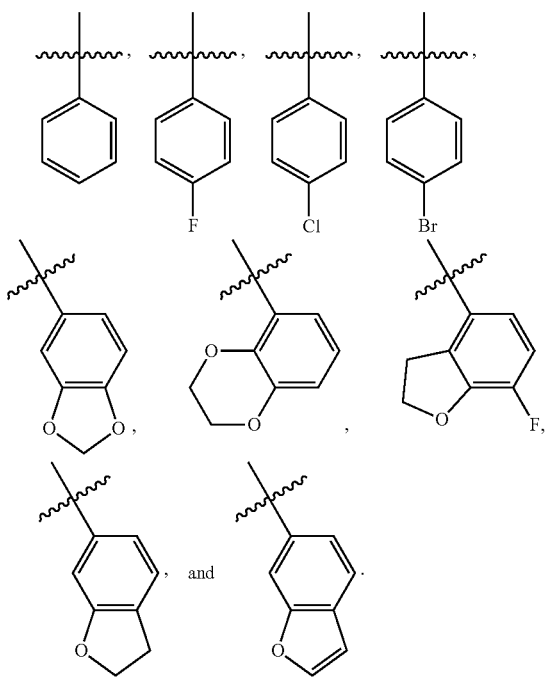

As used herein, the term "aralkyl" represents group R'R"—, wherein R' is an aryl group as defined herein, and R" is an alkylene group as defined herein. It is to be understood that the point of attachment of the aralkyl moiety would be at the alkylene group. Normally, the aryl group may contain 6-14 carbon atoms, and the alkyl group may contain 1-6 carbon atoms. Exemplary aralkyl includes, but is not limited to benzyl, 4-fulorobenzyl, phenylethyl, phenylpropyl, and phenylbutyl.

As used herein, the term "aryloxy" represents —O—R, and R is an aryl group as defined above.

As used herein, the term "arylcarbonyl" represents a group of formula —C(=O)Ar, wherein Ar is an aryl group as defined above.

As used herein, the term "heterocyclyl" refers to a 3-16 membered saturated or unsaturated ring containing 1-4 (e.g., one, two, three, or four) heteroatoms selected from N, O, S, and P, with the remaining atoms as carbon atoms. In particular, a 3-10 membered heterocyclyl is a group having 3-10 carbon atoms as well as heteroatoms in its rings, such as, but not limited to, oxiranyl, aziridinyl, azetidinyl, oxetanyl tetrahydrofuranyl, dioxolinyl, pyrrolidinyl, pyrrolidinonyl, imidazolidinyl, pyrazolidinyl, pyrrolinyl, tetrahydropyranyl, piperidinyl, morpholinyl, dithianyl, thiomorpholinyl, piperazinyl, or trithianyl.

As used herein, the term "heteroaryl" refers to a cyclic aromatic group having 1 to 3 heteroatoms selected from N, O and S atoms as ring atoms, with the remaining ring atoms as carbon atoms, wherein the ring is a 4-16 membered monocycle or fused ring, preferably a 5-12 membered monocycle or fused ring, or a 5-8 membered monocycle or fused ring. Examples of a heteroaryl group include, but are not limited to, furyl, thienyl, oxazolyl, isoxazolyl, thiazolyl, isothiazolyl, oxadiazolyl, triazolyl, thiadiazolyl, pyridyl, pyrrolyl, pyrazolyl, N-alkylpyrrolyl, pyrimidinyl, pyrazinyl, imidazolyl, pyridazinyl, phthalazinyl, phthalazin-1-(2H)-1-yl, pyrido[3,2-d]pyridazin-5(6H)-8-yl, triazinyl, etc., as well as benzo derivatives thereof.

As used herein, the term "heteroarylcarbonyl" is defined similar to the definition of "arylcarbonyl group", and represents a group of formula —C(=O)R, wherein R is a heteroaryl group as defined above.

As used herein, the term "heteroaryloxy" represents a group of formula heteroaryl-O—, wherein the heteroaryl group is as defined above.

As used herein, the term "sulfonamido" represents a group of formula —SO$_2$NR'R", wherein R' and R" are the same or different, and are each independently hydrogen or an alkyl or cycloalkyl group as defined above.

As used herein, the term "carboxyl" represents a group of formula —COOH, and the term "carboxylate" represents —COOR, wherein R each independently represents an alkyl group as defined above.

In the general formula or specific compounds of the present invention, a group, or an atom, or a radical each includes a group, or an atom, or a radical with substitution of an isotope, for example, "hydrogen" includes H, $^2$H (deuterium), or $^3$H (tritium); a $C_{1-14}$ alkyl group includes an alkyl group wherein one or more, or all of the carbon atoms are $^{12}$C, $^{13}$C, or $^{14}$C; and further exemplary examples include isotopes of N, P, or 0.

As used herein, the term "pharmaceutically acceptable carrier" refers to inactive ingredients in a pharmaceutical composition or a pharmaceutical preparation that do not cause significant irritation and do not interfere with the nature of the biologically active compounds applied in an organism, and it includes a diluent, adjuvant, excipient or equivalent pharmaceutically acceptable medium administered together with a therapeutic agent.

As used herein, the term "excipient" refers to a substance for the preparation of a pharmaceutical composition, and it is generally safe, non-toxic, and neither biologically nor otherwise undesirable, and includes various excipients suitable for veterinary use as well as human pharmaceutical use.

The pharmaceutically acceptable carrier which can be employed in the pharmaceutical composition of the present invention includes, but is not limited to sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g. Remington's Pharmaceutical Sciences (1990).

As used herein, the term "formulation" or "dosage form" shall include solid, semi-solid, liquid, or gas formulations. The formulation or dosage form includes, but is not limited to, tablets, capsules, lozenges, hard candies, powders, sprays, creams, salves, suppositories, gels, pastes, lotions, ointments, aqueous suspensions, injectable solutions, elixirs, syrups, and the like. Those skilled in the art will appreciate that, depending on the desired dose and pharmacokinetic parameters, the compound of the present invention may be prepared as different formulations.

The unit dosage range of the compound of the present invention is 0.1-1000 mg, preferred unit dosage range is 1-800 mg, more preferred unit dosage range is 10-600 mg, particularly preferred unit dosage range is 50-450 mg, and the most preferred unit dosage range is 100-300 mg. The formulation or dosage form of the present invention may contain a single or multiple unit dosage of the compound of the present invention.

The compound of the present invention is preferably for oral administration. In various situations, other administration routes may be employed or even preferred, such as intravenous, intraarterial, subcutaneous, intraperitoneal, intramuscular, or transdermal administration, or administration via buccal, nasal, transmucosal, topical, route, as an ophthalmic formulation, or via inhalation. Transdermal administration may be very desirable for patients who are forgetful or petulant about taking oral medicine. The compound of the present invention may also be administered by the percutaneous, intramuscular, intranasal or intrarectal route in particular circumstances. The route of administration may be varied in any way, depending on the physical properties of the drugs, the convenience of the patient and the caregiver, and other relevant conditions (Remington's Pharmaceutical Sciences, 18th Edition, Mack Publishing Co. (1990)).

In another aspect, the present invention provides use of the compound of the present invention for simultaneous, separate or sequential administration in combination with an additional therapeutic agent (such as an additional anti-cancer/anti-tumor agent, or an additional anti-viral agent).

The dosage range of the compound of the present invention or a product comprising the same (such as a pharmaceutical composition, a pharmaceutical formulation, or a dosage form) is 0.1-1000 mg/kg body weight per day, preferred dosage range is 1-800 mg/kg body weight per day, preferred dosage range is 10-600 mg/kg body weight per day, particularly preferred dosage range is 100-400 mg/kg body weight per day, and most preferred dosage range is 120-250 mg/kg body weight per day. The exact dosage required for treating a patient may be determined by a physician in view of the stage and severity of the disease as well as patient's specific need and response.

Unless otherwise indicated, the term "treating" or "treatment", as used herein, means reversing, alleviating, inhibiting the progress of, or preventing the disorder or condition to which such term applies, or one or more symptoms of such disorder or condition.

As used herein, the term "mammal" includes a human or non-human animal. An exemplary human subject includes a human subject having a disease or disorder (such as one described herein) (referred to as a patient), or a normal subject. The term "non-human animal" as used herein includes non-human primates, livestock and/or domesticated animals, such as sheep, dog, cat, cow, pig and the like.

EXAMPLES

The present invention is further described in detail with reference to the following examples and specific embodiments. However, it should not be construed that the scope of the present invention is merely limited to the following examples, technical solutions achieved based on the contents of the present invention are all within the scope of the present invention.

The abbreviations as used herein have the following meanings:

| Abbreviation | Meaning |
| --- | --- |
| AcOH | acetic acid |
| AcOK | potassium acetate |
| $Ac_2O$ | acetic anhydride |
| aq. | aqueous solution |
| $BCl_3$ | boron trichloride |
| BnBr | benzyl bromide |
| BzCl | benzoyl chloride |
| $Bz_2O$ | benzoic anhydride |
| m-CPBA | metachloroperbenzoic acid |
| DAST | diethylaminosulfurtrifluoride |
| DCE | dichloroethane |
| DCM | dichloromethane |
| DMAP | 4-dimethylaminopyridine |
| DMF | N,N-dimethylformamide |
| DMSO | dimethyl sulfoxide |
| $Et_3N$ | triethylamine |
| HBr | hydrogen bromide |
| HCl | hydrochloric acid |
| $H_2O$ | water |
| HPLC | high-performance liquid chromatography |
| $H_2SO_4$ | sulphuric acid |
| KF | potassium fluoride |
| MeOH | methanol |
| MsCl | methylsulfonyl chloride |
| $NaBH_4$ | sodium borohydride |
| NaH | sodium hydride |
| $Na_2S$ | sodium sulfide |
| $NH_3$ | amonia |
| $NaIO_4$ | sodium periodate |
| NaOMe | sodium methoxide |
| $SO_2Cl_2$ | sulfonyl chloride |
| TBAF | tetrabutylammonium fluoride |
| TBDPSCl | tert-butyldiphenylchlorosilane |
| TFA | trifluoroacetic acid |
| THF | tetrahydrofuran |
| TMSOTf | trimethylsilyl triflate |

Example 1

Preparation of (S)-ethyl 2-(((((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)propanoate (C1)

(1) Preparation of 1-((2R,3S,4S,5R)-3-fluoro-4-hydroxy-5-(hydroxymethyl)tetrahydrothiophen-2-yl)cytosine (Compound A, i.e. the core compound)

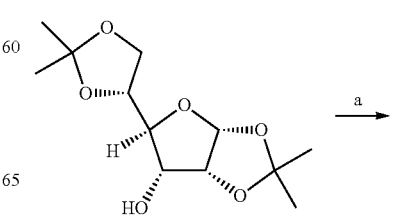

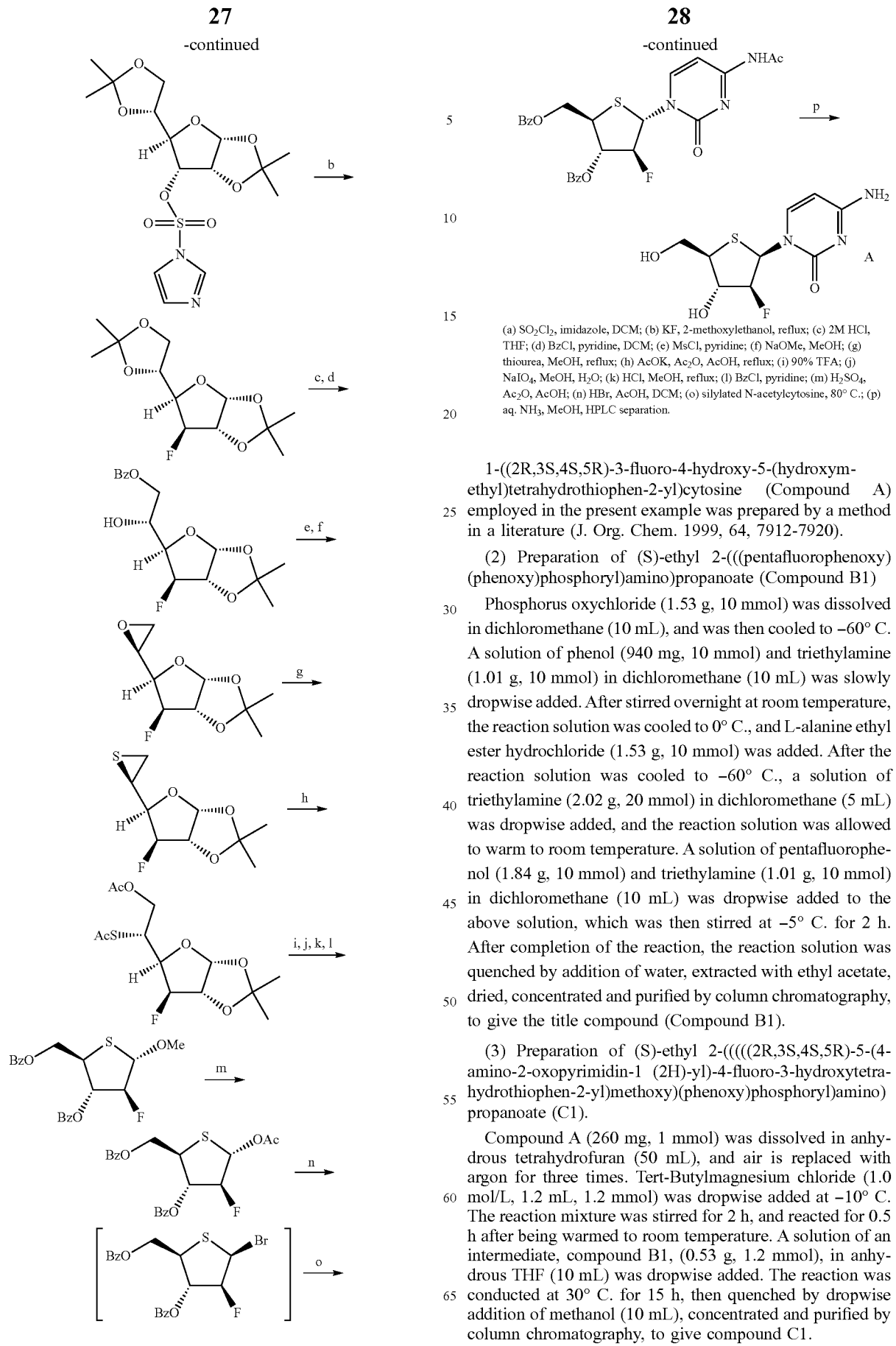

(a) SO₂Cl₂, imidazole, DCM; (b) KF, 2-methoxylethanol, reflux; (c) 2M HCl, THF; (d) BzCl, pyridine, DCM; (e) MsCl, pyridine; (f) NaOMe, MeOH; (g) thiourea, MeOH, reflux; (h) AcOK, Ac₂O, AcOH, reflux; (i) 90% TFA; (j) NaIO₄, MeOH, H₂O; (k) HCl, MeOH, reflux; (l) BzCl, pyridine; (m) H₂SO₄, Ac₂O, AcOH; (n) HBr, AcOH, DCM; (o) silylated N-acetylcytosine, 80° C.; (p) aq. NH₃, MeOH, HPLC separation.

1-((2R,3S,4S,5R)-3-fluoro-4-hydroxy-5-(hydroxymethyl)tetrahydrothiophen-2-yl)cytosine (Compound A) employed in the present example was prepared by a method in a literature (J. Org. Chem. 1999, 64, 7912-7920).

(2) Preparation of (S)-ethyl 2-(((pentafluorophenoxy)(phenoxy)phosphoryl)amino)propanoate (Compound B1)

Phosphorus oxychloride (1.53 g, 10 mmol) was dissolved in dichloromethane (10 mL), and was then cooled to −60° C. A solution of phenol (940 mg, 10 mmol) and triethylamine (1.01 g, 10 mmol) in dichloromethane (10 mL) was slowly dropwise added. After stirred overnight at room temperature, the reaction solution was cooled to 0° C., and L-alanine ethyl ester hydrochloride (1.53 g, 10 mmol) was added. After the reaction solution was cooled to −60° C., a solution of triethylamine (2.02 g, 20 mmol) in dichloromethane (5 mL) was dropwise added, and the reaction solution was allowed to warm to room temperature. A solution of pentafluorophenol (1.84 g, 10 mmol) and triethylamine (1.01 g, 10 mmol) in dichloromethane (10 mL) was dropwise added to the above solution, which was then stirred at −5° C. for 2 h. After completion of the reaction, the reaction solution was quenched by addition of water, extracted with ethyl acetate, dried, concentrated and purified by column chromatography, to give the title compound (Compound B1).

(3) Preparation of (S)-ethyl 2-(((((2R,3S,4S,5R)-5-(4-amino-2-oxopyrimidin-1 (2H)-yl)-4-fluoro-3-hydroxytetrahydrothiophen-2-yl)methoxy)(phenoxy)phosphoryl)amino)propanoate (C1).

Compound A (260 mg, 1 mmol) was dissolved in anhydrous tetrahydrofuran (50 mL), and air is replaced with argon for three times. Tert-Butylmagnesium chloride (1.0 mol/L, 1.2 mL, 1.2 mmol) was dropwise added at −10° C. The reaction mixture was stirred for 2 h, and reacted for 0.5 h after being warmed to room temperature. A solution of an intermediate, compound B1, (0.53 g, 1.2 mmol), in anhydrous THF (10 mL) was dropwise added. The reaction was conducted at 30° C. for 15 h, then quenched by dropwise addition of methanol (10 mL), concentrated and purified by column chromatography, to give compound C1.

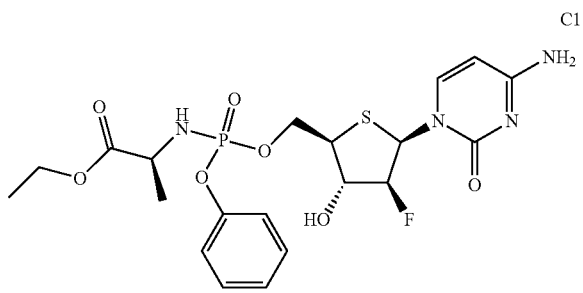 [SMILES: CCOC(=O)[C@H](C)NP(=O)(OC[C@H]1S[C@@H](n2ccc(N)nc2=O)[C@@H](F)[C@@H]1O)Oc1ccccc1]

C1

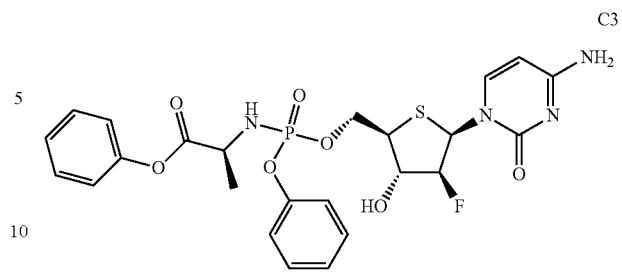

C3

The data for structural characterization of the compound are as follows.

ESI-MS: 517.7 (M+1)

$^1$H NMR (DMSO-$d_6$, 400 MHz) δ 7.86 (d, J=3.4 Hz, 1H), 7.38 (t, J=7.6 Hz, 2H), 7.31-7.17 (m, 5H), 6.56 (dd, J=4 Hz, 14 Hz, 1H), 6.09-6.03 (m, 2H), 5.77 (d, J=7.6 Hz, 1H), 5.03-4.87 (m, 2H), 4.36-4.32 (m, 2H), 4.14-4.12 (m, 3H), 3.80-3.78 (m, 1H), 1.28-1.23 (m, 6H).

The data for structural characterization of the compound are as follows.

ESI-MS: 565.1 (M+1)

$^1$H NMR (DMSO-$d_6$, 400 MHz) δ 7.86 (d, J=3.4 Hz, 1H), 7.38 (t, J=7.6 Hz, 2H), 7.31-7.17 (m, 10H), 6.56 (dd, J=4 Hz, 14 Hz, 1H), 6.09-6.03 (m, 2H), 5.77 (d, J=7.6 Hz, 1H), 5.03-4.87 (m, 2H), 4.36-4.32 (m, 2H), 4.14-4.12 (m, 1H), 3.80-3.78 (m, 1H), 1.23 (d, J=6.4 Hz, 3H).

Example 2

Preparation of (S)-benzyl 2-(((((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)propanoate (C2)

Compound C2 was prepared according to a method similar to that of Example 1, using phosphorus oxychloride, phenol, L-alanine benzyl ester hydrochloride, pentafluorophenol, and Compound A as starting materials.

Example 4

Preparation of (S)-isopropyl 2-(((((2R,3S,4S,5R)-5-(4-amino-2-oxopyrimidin-1 (2H)-yl)-4-fluoro-3-hydroxytetrahydrothiophen-2-yl)methoxy) (4-fluorophenoxy)phosphoryl)amino)propanoate (C4)

(1) Preparation of (S)-isopropyl 2-(((pentafluorophenoxy)(4-fluorophenoxy)phosphoryl)amino)propanoate.

Phosphorus oxychloride (1.53 g, 10 mmol) was dissolved in dichloromethane (10 mL), and was then cooled to −60° C. A solution of 4-fluorophenol (1.12 g, 10 mmol) and triethylamine (1.01 g, 10 mmol) in dichloromethane (10 mL) was slowly dropwise added. After stirred overnight at room temperature, the reaction solution was cooled to 0° C., and L-alanine isopropyl ester hydrochloride (1.53 g, 10 mmol) was added. After the reaction solution was cooled to −60° C., a solution of triethylamine (2.02 g, 20 mmol) in dichloromethane (5 mL) was dropwise added, and the reaction solution was allowed to warm to room temperature. A solution of pentafluorophenol (1.84 g, 10 mmol) and triethylamine (1.01 g, 10 mmol) in dichloromethane (10 mL) was dropwise added to the above solution, which was then stirred at −5° C. for 2 h. After completion of the reaction, the reaction solution was quenched by addition of water, extracted with ethyl acetate, dried, concentrated and purified by column chromatography, to give the title compound.

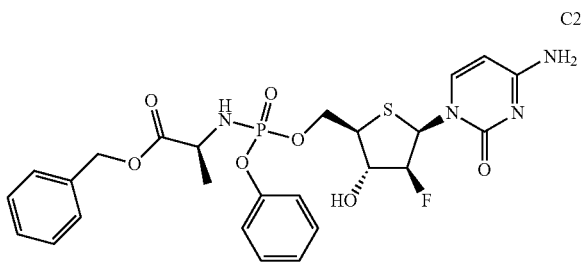 [SMILES: C[C@H](NP(=O)(OC[C@H]1S[C@@H](n2ccc(N)nc2=O)[C@@H](F)[C@@H]1O)Oc1ccccc1)C(=O)OCc1ccccc1]

C2

The data for structural characterization of the compound are as follows.

ESI-MS: 579.6 (M+1)

$^1$H NMR (DMSO-$d_6$, 400 MHz) δ 7.86 (d, J=3.4 Hz, 1H), 7.38 (t, J=7.6 Hz, 2H), 7.31-7.17 (m, 10H), 6.56 (dd, J=4 Hz, 14 Hz, 1H), 6.09-6.03 (m, 2H), 5.77 (d, J=7.6 Hz, 1H), 5.36 (s, 2H), 5.03-4.87 (m, 2H), 4.36-4.32 (m, 2H), 4.14-4.12 (m, 1H), 3.80-3.78 (m, 1H), 1.23 (d, J=6.4 Hz, 3H).

Example 3

Preparation of (S)-phenyl 2-(((((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)propanoate (C3)

Compound C3 was prepared according to a method similar to that of Example 1, using phosphorus oxychloride, phenol, L-alanine phenyl ester hydrochloride, pentafluorophenol, and Compound A as starting materials.

(2) Preparation of (S)-isopropyl 2-(((((2R,3 S,4S,5R)-5-(4-amino-2-oxopyrimidin-1(2H)-yl)-4-fluoro-3-hydroxytetrahydrothiophen-2-yl)methoxy)(4-fluorophenoxy)phosphoryl)amino)propanoate (C4).

Compound A (260 mg, 1 mmol) was dissolved in anhydrous tetrahydrofuran (50 mL), and air is replaced with argon for three times. Tert-Butylmagnesium chloride (1.0 mol/L, 1.2 mL, 1.2 mmol) was dropwise added at −10° C. The reaction mixture was stirred for 2 h, and reacted for 0.5 h after being warmed to room temperature. A solution of (S)-isopropyl 2-(((pentafluorophenoxy)(4-fluorophenoxy)phosphoryl)amino)propanoate (566 mg, 1.2 mmol) in anhydrous THF (10 mL) was dropwise added. The reaction was conducted at 30° C. for 15 h, then quenched by dropwise addition of methanol (10 mL), concentrated and purified by column chromatography, to give compound C4.

C4

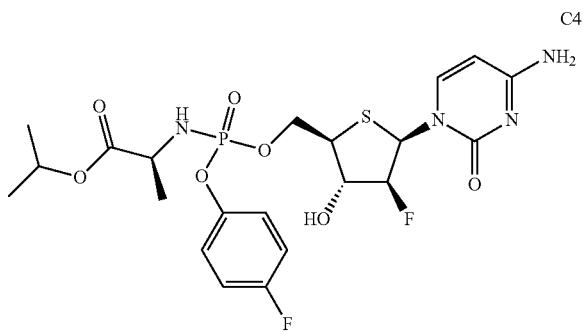 [SMILES: CC(C)OC(=O)[C@H](C)NP(=O)(OC[C@H]1S[C@@H](n2ccc(N)nc2=O)[C@@H](F)[C@@H]1O)Oc1ccc(F)cc1]

The data for structural characterization of the compound are as follows.

ESI-MS: 549.3 (M+1)

$^1$H NMR (DMSO-d$_6$, 400 MHz) δ 7.86 (d, J=3.4 Hz, 1H), 7.38 (t, J=7.6 Hz, 2H), 7.35-7.17 (m, 4H), 6.56 (dd, J=4 Hz, 14 Hz, 1H), 6.09-6.03 (m, 2H), 5.77 (d, J=7.6 Hz, 1H), 5.03-4.87 (m, 2H), 4.36-4.32 (m, 2H), 4.14-4.12 (m, 1H), 3.80-3.78 (m, 1H), 1.23 (d, J=6.4 Hz, 3H).

Example 5

Preparation of (S)-isopropyl 2-(((((2R,3S,4S,5R)-5-(4-amino-2-oxopyrimidin-1(2H)-yl)-4-fluoro-3-hydroxytetrahydrothiophen-2-yl)methoxy)(4-chlorophenoxy)phosphoryl)amino)propanoate (C5)

Compound C5 was prepared according to a method similar to that of Example 1, using phosphorus oxychloride, 4-chlorophenol, L-alanine isopropyl ester hydrochloride, pentafluorophenol, and Compound A as starting materials.

C5

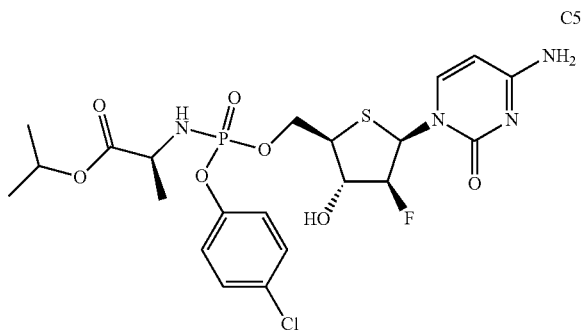 [SMILES: CC(C)OC(=O)[C@H](C)NP(=O)(OC[C@H]1S[C@@H](n2ccc(N)nc2=O)[C@@H](F)[C@@H]1O)Oc1ccc(Cl)cc1]

The data for structural characterization of the compound are as follows.

ESI-MS: 565.4 (M+1)

$^1$H NMR (DMSO-d$_6$, 400 MHz) δ 7.86 (d, J=3.4 Hz, 1H), 7.38 (t, J=7.6 Hz, 2H), 7.30-7.17 (m, 4H), 6.56 (dd, J=4 Hz, 14 Hz, 1H), 6.09-6.03 (m, 2H), 5.77 (d, J=7.6 Hz, 1H), 5.03-4.87 (m, 2H), 4.36-4.32 (m, 2H), 4.14-4.12 (m, 1H), 3.80-3.78 (m, 1H), 1.23 (d, J=6.4 Hz, 3H).

Example 6

Preparation of (S)-isopropyl 2-(((((2R,3S,4S,5R)-5-(4-amino-2-oxopyrimidin-1 (2H)-yl)-4-fluoro-3-hydroxytetrahydrothiophen-2-yl)methoxy)(4-bromophenoxy)phosphoryl)amino)propanoate (C6)

Compound C6 was prepared according to a method similar to that of Example 1, using phosphorus oxychloride, 4-bromophenol, L-alanine isopropyl ester hydrochloride, pentafluorophenol, and Compound A as starting materials.

C6

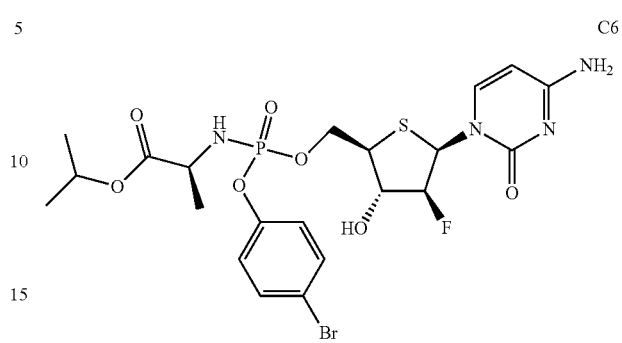

The data for structural characterization of the compound are as follows.

ESI-MS: 611.2 (M+1)

$^1$H NMR (DMSO-d$_6$, 400 MHz) δ 7.86 (d, J=3.4 Hz, 1H), 7.38 (t, J=7.6 Hz, 2H), 7.28-7.17 (m, 4H), 6.56 (dd, J=4 Hz, 14 Hz, 1H), 6.09-6.03 (m, 2H), 5.77 (d, J=7.6 Hz, 1H), 5.03-4.87 (m, 2H), 4.36-4.32 (m, 2H), 4.14-4.12 (m, 1H), 3.80-3.78 (m, 1H), 1.23 (d, J=6.4 Hz, 3H).

Example 7

Preparation of isopropyl 2-(((((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)-2-methylpropanoate (C7)

(1) Preparation of isopropyl 2-methyl-2-(((pentafluorophenoxy)(phenoxy)phosphoryl)amino)propanoate.

Phosphorus oxychloride (1.53 g, 10 mmol) was dissolved in dichloromethane (10 mL), and was then cooled to −60° C. A solution of phenol (1.12 g, 10 mmol) and triethylamine (1.01 g, 10 mmol) in dichloromethane (10 mL) was slowly dropwise added. After stirred overnight at room temperature, the reaction solution was cooled to 0° C., and 2-methylalanine isopropyl ester hydrochloride (1.82 g, 10 mmol) was added. After the reaction solution was cooled to −60° C., a solution of triethylamine (2.02 g, 20 mmol) in dichloromethane (5 mL) was dropwise added, and the reaction solution was allowed to warm to room temperature. A solution of pentafluorophenol (1.84 g, 10 mmol) and triethylamine (1.01 g, 10 mmol) in dichloromethane (10 mL) was dropwise added to the above solution, which was then stirred at −5° C. for 2 h. After completion of the reaction, the reaction solution was quenched by addition of water, extracted with ethyl acetate, dried, concentrated and purified by column chromatography, to give the title compound.

(2) Preparation of isopropyl 2-(((((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)-2-methylpropanoate (C7).

Compound A (260 mg, 1 mmol) was dissolved in anhydrous tetrahydrofuran (50 mL), and air is replaced with argon for three times. Tert-Butylmagnesium chloride (1.0 mol/L, 1.2 mL, 1.2 mmol) was dropwise added at −10° C. The reaction mixture was stirred for 2 h, and reacted for 0.5 h after being warmed to room temperature. A solution of isopropyl 2-methyl-2-(((pentafluorophenoxy)(phenoxy)phosphoryl)amino)propanoate (582 mg, 1.2 mmol) in anhydrous THF (10 mL) was dropwise added. The reaction was conducted at 30° C. for 15 h, then quenched by dropwise addition of methanol (10 mL), concentrated and purified by column chromatography, to give compound C7.

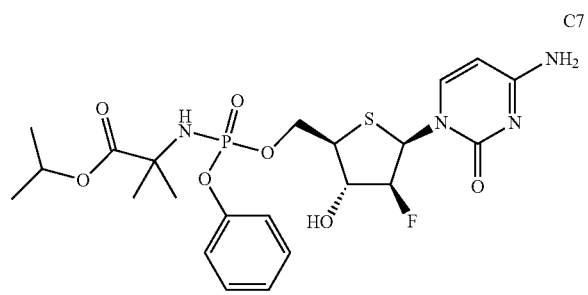 [SMILES: CC(C)OC(=O)C(C)(C)NP(=O)(OC[C@H]1S[C@@H](n2ccc(N)nc2=O)[C@@H](F)[C@@H]1O)Oc1ccccc1]

The data for structural characterization of the compound are as follows.

ESI-MS: 545.5 (M+1)

$^1$H NMR (DMSO-d$_6$, 400 MHz) δ 7.86 (d, J=3.4 Hz, 1H), 7.38 (t, J=7.6 Hz, 2H), 7.31-7.17 (m, 5H), 6.56 (dd, J=4 Hz, 14 Hz, 1H), 6.09-6.03 (m, 2H), 5.77 (d, J=7.6 Hz, 1H), 5.03-4.87 (m, 2H), 4.36-4.32 (m, 2H), 4.14-4.12 (m, 1H), 1.27 (s, 6H), 1.17 (d, J=5.2 Hz, 6H).

Example 8

Preparation of (S)-isopropyl 2-(((S)-(((2R,3S,4S, 5R)-5-(4-amino-2-oxopyrimidin-1(2H)-yl)-4-fluoro-3-hydroxytetrahydrothiophen-2-yl)methoxy)(phenoxy)phosphoryl)amino)propanoate (C8)

(S)-isopropyl 2-(((S)-(pentafluorophenoxy)(phenoxy)phosphoryl)amino)propanoate employed in the present invention was prepared by a method in a literature (*J. Org. Chem.* 2011, 76, 8311-8319).

Compound C8 was prepared according to a method similar to that of Example 1, using (S)-isopropyl 2-(((S)-(pentafluorophenoxy)(phenoxy)phosphoryl)amino)propanoate, and Compound A as starting materials.

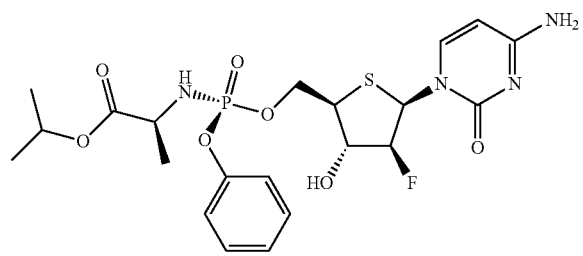

The data for structural characterization of the compound are as follows.

ESI-MS: 531.1 (M+1)

$^1$H NMR (DMSO-d$_6$, 400 MHz) δ 7.86 (d, J=3.4 Hz, 1H), 7.38 (t, J=7.6 Hz, 2H), 7.31-7.17 (m, 5H), 6.56 (dd, J=4 Hz, 14 Hz, 1H), 6.09-6.03 (m, 2H), 5.77 (d, J=7.6 Hz, 1H), 5.03-4.87 (m, 2H), 4.36-4.32 (m, 2H), 4.14-4.12 (m, 1H), 3.80-3.78 (m, 1H), 1.23 (d, J=6.4 Hz, 3H), 1.17 (d, J=5.2 Hz, 6H).

Example 9

Preparation of (S)-isopropyl 2-(((S)-(((2R,3S,4S, 5R)-5-(4-amino-5-fluoro-2-oxopyrimidin-1(2H)-yl)-4-fluoro-3-hydroxytetrahydrothiophen-2-yl) methoxy)(phenoxy)phosphoryl)amino)propanoate (C9)

1-((2R,3S,4S,5R)-3-fluoro-4-hydroxy-5-(hydroxymethyl)tetrahydrothiophen-2-yl)-5-fluorocytosine employed in the present invention was prepared by a method in a literature (*Bioorg. Med. Chem.* 2000, 8, 1545-1558).

Compound C9 was prepared according to a method similar to that of Example 1, using (S)-isopropyl 2-(((S)-(pentafluorophenoxy)(phenoxy)phosphoryl)amino)propanoate, and 1-((2R,3S,4S,5R)-3-fluoro-4-hydroxy-5-(hydroxymethyl)tetrahydrothiophen-2-yl)-5-fluorocytosine as starting materials.

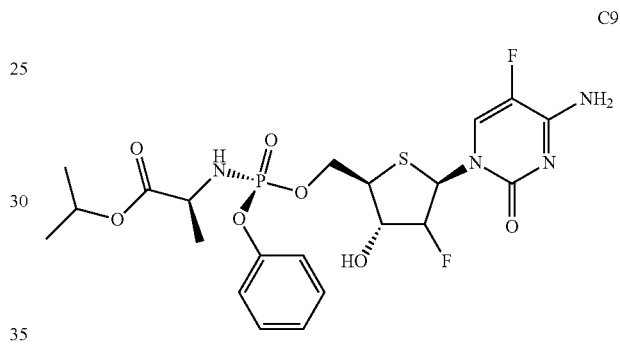

The data for structural characterization of the compound are as follows.

ESI-MS: 549.5 (M+1)

$^1$H NMR (DMSO-d$_6$, 400 MHz) δ 8.23 (d, J=7.3 Hz, 1H), 7.38-7.31 (m, 3H), 7.23-7.16 (m, 5H), 6.52 (dd, J=4 Hz, 14 Hz, 1H), 6.05-6.03 (m, 2H), 5.03-4.87 (m, 2H), 4.36-4.32 (m, 2H), 4.14-4.12 (m, 1H), 3.80-3.78 (m, 1H), 1.25 (d, J=6.4 Hz, 3H), 1.14 (d, J=5.2 Hz, 6H).

Example 10

Preparation of (S)-isopropyl 2-(((S)-(((2R,3S,4S, 5R)-5-(6-amino-2-chloro-9H-purin-9-yl)-4-fluoro-3-hydroxytetrahydrothiophen-2-yl)methoxy)(phenoxy) phosphoryl)amino)propanoate (C10)

(2R,3S,4S,5R)-5-(6-amino-2-chloro-9H-purin-9-yl)-4-fluoro-2-(hydroxymethyl)tetrahydrothiophen-3-ol employed in the present invention was prepared by a method in a literature (*Bioorg. Med. Chem.* 2000, 8, 1545-1558).

Compound C10 was prepared according to a method similar to that of Example 1, using (S)-isopropyl 2-(((S)-(pentafluorophenoxy)(phenoxy)phosphoryl)amino)propanoate, and (2R,3S,4S,5R)-5-(6-amino-2-chloro-9H-purin-9-yl)-4-fluoro-2-(hydroxymethyl)tetrahydrothiophen-3-ol as starting materials.

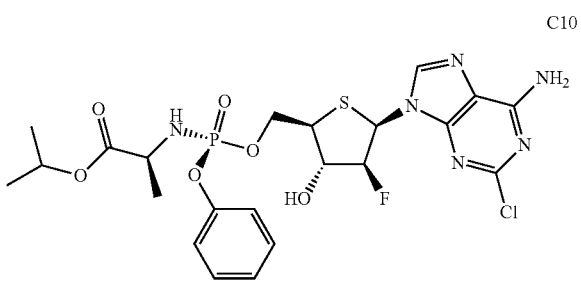 [SMILES: CC(C)OC(=O)[C@H](C)N[P@](=O)(OC[C@H]1S[C@@H](n2cnc3c(N)nc(Cl)nc32)[C@@H](F)[C@@H]1O)Oc1ccccc1]

The data for structural characterization of the compound are as follows.

ESI-MS: 589.4 (M+1)

$^1$H NMR (DMSO-d$_6$, 400 MHz) δ 8.42 (s, 1H), 7.32-7.15 (m, 8H), 6.50 (dd, J=4 Hz, 14 Hz, 1H), 6.07-6.03 (m, 2H), 5.72 (d, J=7.6 Hz, 1H), 5.01-4.87 (m, 2H), 4.37-4.32 (m, 2H), 4.15-4.12 (m, 1H), 3.80-3.78 (m, 1H), 1.24 (d, J=6.4 Hz, 3H), 1.15 (d, J=5.2 Hz, 6H).

Example 11

Preparation of (S)-isopropyl 2-(((S)-(((2R,3S,4S,5R)-5-(4-(2-propylpentanamido)-2-oxopyrimidin-1(2H)-yl)-4-fluoro-3-hydroxytetrahydrothiophen-2-yl)methoxy)(phenoxy)phosphoryl)amino)propanoate (C11)

Compound C8 (53 mg, 0.1 mmol) and ethyldiisopropylamine (26 mg, 0.2 mmol) was dissolved in dry dichloromethane (2 mL). 2-propylpentanoyl chloride (17 mg, 0.1 mmol) was added at 0° C. The reaction mixture was warmed to room temperature, and stirred overnight. The reaction mixture was quenched by addition of saturated NaHCO$_3$, extracted with ethyl acetate, dried, concentrated, and purified by column chromatography, to give compound C11.

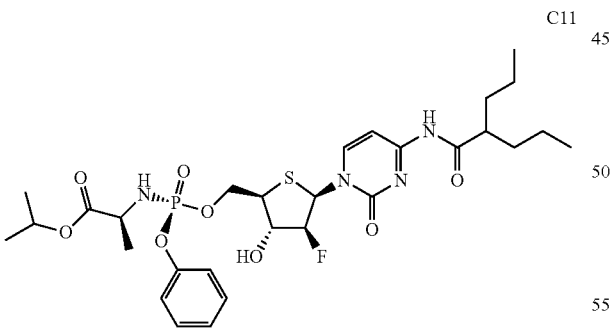

The data for structural characterization of the compound are as follows.

ESI-MS: 657.7 (M+1)

$^1$H NMR (DMSO-d$_6$, 400 MHz) δ 7.86 (d, J=3.4 Hz, 1H), 7.38 (t, J=7.6 Hz, 2H), 7.31-7.17 (m, 5H), 6.56 (dd, J=4 Hz, 14 Hz, 1H), 6.09-6.03 (m, 2H), 5.77 (d, J=7.6 Hz, 1H), 5.03-4.87 (m, 2H), 4.36-4.32 (m, 2H), 4.14-4.12 (m, 1H), 3.80-3.78 (m, 1H), 2.50-2.47 (m, 1H), 1.43-1.22 (m, 17H), 0.94-0.91 (m, 6H).

Example 12

Preparation of (S)-isopropyl 2-(((S)-(((2R,3S,5R)-5-(4-amino-2-oxopyrimidin-1(2H)-yl)-4,4-difluoro-3-hydroxytetrahydrothiophen-2-yl)methoxy)(phenoxy)phosphoryl)amino)propanoate (C12)

(1) Preparation of 1-((2R,4S,5R)-3,3-difluoro-4-hydroxy-5-(hydroxymethyl)tetrahydrothiophen-2-yl)cytosine

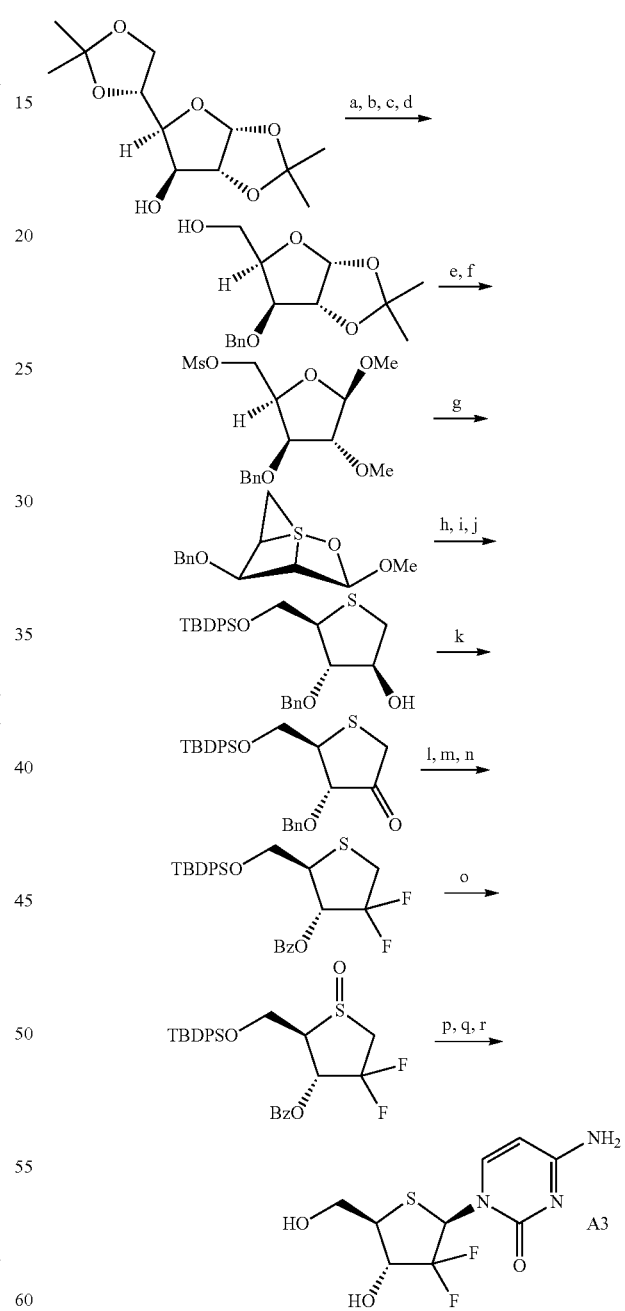

(a) BnBr, NaH, DMF, THF; (b) 2M HCl, THF; (c) NaIO$_4$, H$_2$O, MeOH; (d) NaBH$_4$, MeOH; (e) 5% HCl/MeOH; (f) MsCl, pyridine; (g) Na$_2$S, DMF, 100° C.; (h) 4M HCl, THF; (i) NaBH$_4$, MeOH; (j) TBDPSCl, imidazole, DMF; (k) Ac$_2$O, DMSO; (l) DAST, DCM; (m) BCl$_3$, DCM, -78° C.; (n) Bz$_2$O, Et$_3$N, DMAP, CH$_3$CN; (o) m-CPBA, DCM, -78° C.; (p) silylated N-acetylcytosine, TMSOTf, DCE, 0° C.; (q) TBAF, THF; (r) aq. NH$_3$, MeOH, HPLC separation.

1-((2R,4S,5R)-3,3-difluoro-4-hydroxy-5-(hydroxymethyl)tetrahydrothiophen-2-yl)cytosine employed in the present invention was prepared by a method in a literature (*J. Org. Chem.* 1997, 62, 3140-3152).

(2) Compound C12 was prepared according to a method similar to that of Example 1, using (S)-isopropyl 2-(((S)-(pentafluorophenoxy)(phenoxy)phosphoryl)amino)propanoate, and 1-((2R,4S,5R)-3,3-difluoro-4-hydroxy-5-(hydroxymethyl)tetrahydrothiophen-2-yl)cytosine as starting materials.

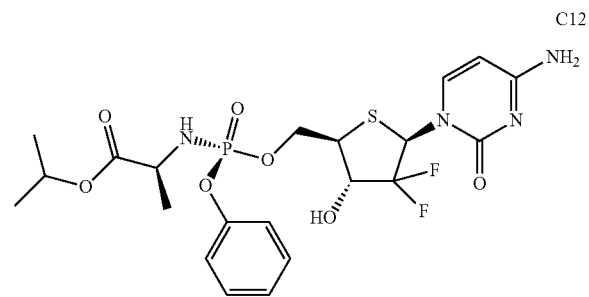 [SMILES: CC(C)OC(=O)[C@H](C)N[P@](=O)(OC[C@H]1S[C@@H](n2ccc(N)nc2=O)C(F)(F)[C@@H]1O)Oc1ccccc1]

C12

The data for structural characterization of the compound are as follows.

ESI-MS: 549.5 (M+1)

$^1$H NMR (DMSO-d$_6$, 400 MHz) δ 7.96 (d, J=3.4 Hz, 1H), 7.35 (m, 3H), 7.23-7.17 (m, 5H), 6.46 (dd, J=4 Hz, 14 Hz, 1H), 5.98-5.95 (m, 2H), 5.84 (d, J=7.6 Hz, 1H), 5.35 (brs, 1H), 4.36-4.32 (m, 2H), 4.17-4.14 (m, 1H), 3.85-3.80 (m, 1H), 1.13 (d, J=6.4 Hz, 3H), 1.09 (d, J=5.2 Hz, 6H).

Examples 13 and 14

Preparation of (S)-isopropyl 2-(((S)-(((2R,3S,4S,5R)-5-(4-amino-2-oxopyrimidin-1(2H)-yl)-4-fluoro-3-hydroxytetrahydrothiophen-2-yl)methoxy)(benzo[d][1,3]dioxol-5-yloxy)phosphoryl)amino) propanoate (C14) and (S)-isopropyl 2-(((R)-(((2R,3S,4S,5R)-5-(4-amino-2-oxopyrimidin-1 (2H)-yl)-4-fluoro-3-hydroxytetrahydrothiophen-2-yl)methoxy)(benzo[d][1,3]dioxol-5-yloxy)phosphoryl)amino) propanoate (C13)

(1) Preparation of (S)-isopropyl 2-(((pentafluorophenoxy)(benzo[d][1,3]dioxol-5-yloxy)phosphoryl)amino)propanoate.

Phosphorus oxychloride (1.53 g, 10 mmol) was dissolved in dichloromethane (10 mL), and was then cooled to −60° C. A solution of sesamol (1.38 g, 10 mmol) and triethylamine (1.01 g, 10 mmol) in dichloromethane (10 mL) was slowly dropwise added. After stirred overnight at room temperature, the reaction solution was cooled to 0° C., and L-alanine isopropyl ester hydrochloride (1.53 g, 10 mmol) was added. After the reaction solution was cooled to −60° C., a solution of triethylamine (2.02 g, 20 mmol) in dichloromethane (5 mL) was dropwise added, and the reaction solution was allowed to warm to room temperature. A solution of pentafluorophenol (1.84 g, 10 mmol) and triethylamine (1.01 g, 10 mmol) in dichloromethane (10 mL) was dropwise added to the above solution, which was then stirred at −5° C. for 2 h. After completion of the reaction, the reaction solution was quenched by addition of water, extracted with ethyl acetate, dried, concentrated and purified by column chromatography, to give the title compound.

(2) Preparation of (S)-isopropyl 2-(((((2R,3 S,4S,5R)-5-(4-amino-2-oxopyrimidin-1 (2H)-yl)-4-fluoro-3-hydroxytetrahydrothiophen-2-yl)methoxy)(benzo[d][1,3]dioxol-5-yloxy)phosphoryl)amino)propanoate.

Compound A (260 mg, 1 mmol) was dissolved in anhydrous tetrahydrofuran (50 mL), and air is replaced with argon for three times. Tert-Butylmagnesium chloride (1.0 mol/L, 1.2 mL, 1.2 mmol) was dropwise added at −10° C. The reaction mixture was stirred for 2 h, and reacted for 0.5 h after being warmed to room temperature. A solution of (S)-isopropyl 2-(((pentafluorophenoxy)(benzo[d][1,3]dioxol-5-yloxy)phosphoryl)amino)propanoate (596 mg, 1.2 mmol) in anhydrous THF (10 mL) was dropwise added. The reaction was conducted at 30° C. for 15 h, then quenched by dropwise addition of methanol (10 mL), concentrated and purified by column chromatography, to give the title compound.

(3) Preparation of (S)-isopropyl 2-(((S)-(((2R,3S,4S,5R)-5-(4-amino-2-oxopyrimidin-1(2H)-yl)-4-fluoro-3-hydroxytetrahydrothiophen-2-yl)methoxy) (benzo[d][1,3]dioxol-5-yloxy)phosphoryl)amino)propanoate (C14) and (S)-isopropyl 2-(((R)-(((2R,3S,4S,5R)-5-(4-amino-2-oxopyrimidin-1 (2H)-yl)-4-fluoro-3-hydroxytetrahydrothiophen-2-yl)methoxy)(benzo[d][1,3] dioxol-5-yloxy)phosphoryl)amino)propanoate (C13).

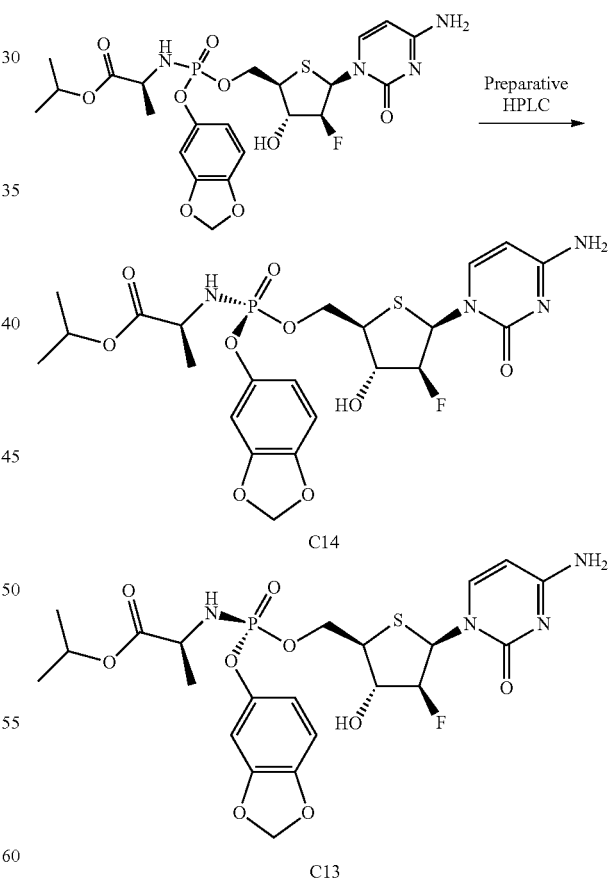

C14

C13

The mixture of the diastereomers obtained in the previous step was separated by preparative HPLC using the following separation conditions: octadecyl bonded silica gel was used as filler (20×250 mm, 5 μm), column temperature was 40° C., flow rate was 10.0 mL/min, detection wavelength was 220 nm, mobile phase A was water (neutral), mobile phase B was methanol, and linear gradient elution was performed. The first main peak was collected, and freeze-dried to obtain (S)-isopropyl 2-(((R)-(((2R,3S,4S,5R)-5-(4-amino-2-oxopyrimidin-1(2H)-yl)-4-fluoro-3-hydroxytetrahydrothiophen-2-yl)methoxy)(benzo[d][1,3]dioxol-5-yloxy)phosphoryl)amino)propanoate (C13), 17 mg; and the second main peak was collected, and freeze-dried to obtain (S)-isopropyl 2-(((S)-(((2R,3S,4S,5R)-5-(4-amino-2-oxopyrimidin-1(2H)-yl)-4-fluoro-3-hydroxytetrahydrothiophen-2-yl)methoxy)(benzo[d][1,3]dioxol-5-yloxy)phosphoryl)amino)propanoate (C14), 30 mg.

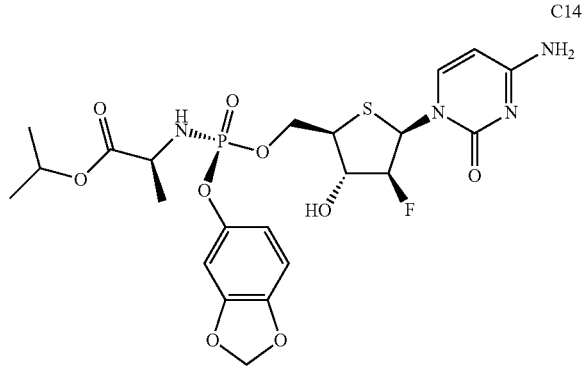 [SMILES: CC(C)OC(=O)[C@H](C)N[P@](=O)(OC[C@H]1S[C@@H](n2ccc(N)nc2=O)[C@@H](F)[C@@H]1O)Oc1ccc2c(c1)OCO2]

C14

The data for structural characterization of the compound are as follows.
ESI-MS: 575.2 (M+1)
$^1$H NMR (DMSO-d$_6$, 400 MHz) δ 7.93 (d, J=8 Hz, 1H), 7.75 (bs, 1H), 7.46 (bs, 1H), 6.88-6.83 (m, 2H), 6.67-6.65 (m, 1H), 6.51 (d, J=8 Hz, 1H), 5.76 (d, J=7.6 Hz, 1H), 4.90-4.86 (m, 4H), 4.31 (bs, 2H), 4.13-4.11 (m, 1H), 3.78-3.76 (m, 1H), 3.50 (bs, 1H), 1.23 (d, J=6.4 Hz, 3H), 1.16 (d, J=5.2 Hz, 6H).
$^{31}$P NMR (DMSO-d$_6$, 162 MHz) δ 4.59.

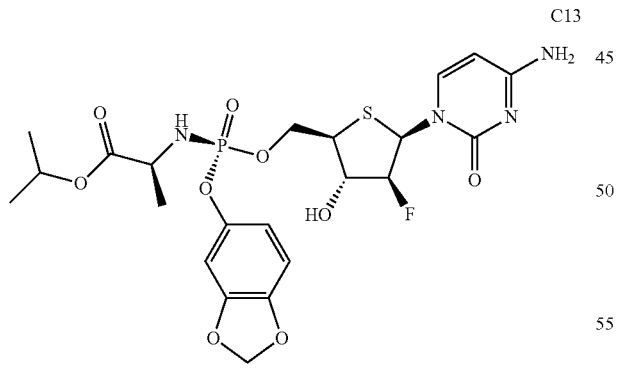

C13

The data for structural characterization of the compound are as follows.
ESI-MS: 575.2 (M+1)
$^1$H NMR (DMSO-d$_6$, 400 MHz) δ 7.93 (d, J=8 Hz, 1H), 7.75 (bs, 1H), 7.46 (bs, 1H), 6.88-6.83 (m, 2H), 6.67-6.65 (m, 1H), 6.51 (d, J=8 Hz, 1H), 5.76 (d, J=7.6 Hz, 1H), 4.90-4.86 (m, 4H), 4.31 (bs, 2H), 4.13-4.11 (m, 1H), 3.78-3.76 (m, 1H), 3.50 (bs, 1H), 1.23 (d, J=6.4 Hz, 3H), 1.16 (d, J=5.2 Hz, 6H). $^{31}$P NMR (DMSO-d$_6$, 162 MHz) δ 4.50.

Example 15

Preparation of (2S)-4-fluorobenzyl 2-(((((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)propanoate (C15)

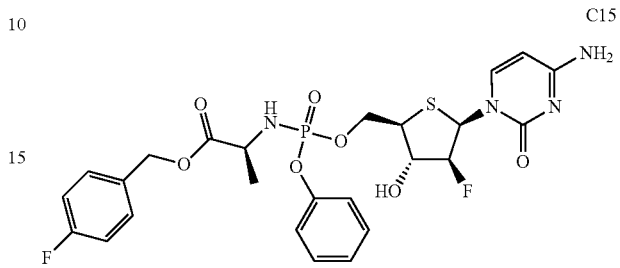

C15

Compound C15 was prepared according to a method similar to that of Example 1, using phosphorus oxychloride, phenol, L-alanine 4-fluorobenzyl ester hydrochloride, pentafluorophenol, and Compound A as starting materials.
The data for structural characterization of the compound are as follows.
ESI-MS: 597.2 (M+1)
$^1$H NMR (DMSO-d$_6$, 400 MHz) δ 7.86 (d, J=8 Hz, 1H), 7.67-7.17 m, 12H), 6.54 (dd, J=4 Hz, 14 Hz, 1H), 6.21-6.15 (m, 1H), 6.07 (bs, 1H), 5.78 (d, J=4 Hz, 1H), 5.11 (bs, 2H), 4.31 (bs, 2H), 4.12-4.10 (m, 1H), 3.94-3.92 (m, 1H), 3.47 (bs, 1H), 1.26 (d, J=8 Hz, 3H).
$^{31}$P NMR (DMSO-d$_6$, 162 MHz) δ 4.02.

Example 16

(S)-isopropyl 2-(((((2R,3S,4S,5R)-5-(4-amino-2-oxopyrimidin-1(2H)-yl)-4-fluoro-3-hydroxytetrahydrothiophen-2-yl)methoxy)((2,3-dihydrobenzo[b][1,4]dioxin-5-yl)oxy)phosphoryl)amino)propanoate (C16)

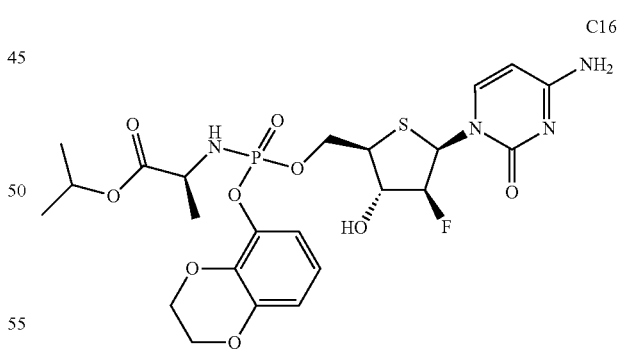

C16

Compound C16 was prepared according to a method similar to that of Example 1, using phosphorus oxychloride, 5-hydroxy-2,3-dihydrobenzo[1,4]dioxine, L-alanine isopropyl ester hydrochloride, pentafluorophenol, and Compound A as starting materials.
The data for structural characterization of the compound are as follows.
ESI-MS: 589.2 (M+1)
$^1$H NMR (DMSO-d$_6$, 400 MHz) δ 7.93 (d, J=8 Hz, 1H), 7.34 (bs, 1H), 7.26 (bs, 1H), 6.91-6.89 (m, 1H), 6.81-6.73

(m, 1H), 6.61-6.56 (m, 1H), 6.11-6.07 (m, 1H), 6.01-5.85 (m, 1H), 5.80-5.75 (m, 1H), 5.04-4.82 (m, 1H), 4.37-4.17 (m, 7H), 3.87-3.83 (m, 1H), 3.50 (bs, 1H), 1.23 (d, J=6.4 Hz, 3H), 1.16 (d, J=5.2 Hz, 6H).
$^{31}$P NMR (DMSO-d$_6$, 162 MHz) δ 4.58.

Example 17

(S)-isopropyl 2-(((((2R,3S,4S,5R)-5-(4-amino-2-oxopyrimidin-1(2H)-yl)-4-fluoro-3-hydroxytetrahydrothiophen-2-yl)methoxy)((7-fluoro-2,3-dihydrobenzofuran-4-yl)oxy)phosphoryl)amino)propanoate (C17)

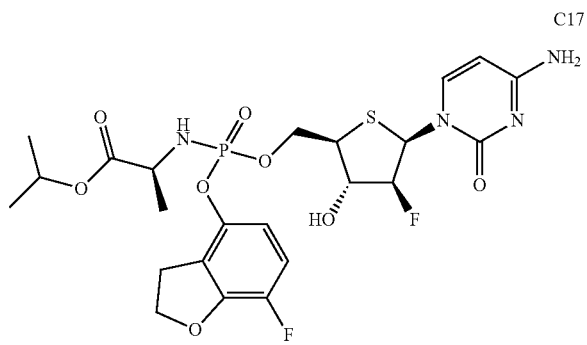 [SMILES: CC(C)OC(=O)[C@H](C)NP(=O)(OC[C@H]1S[C@@H](n2ccc(N)nc2=O)[C@@H](F)[C@@H]1O)Oc1ccc(F)c2c1CCO2]

Compound C17 was prepared according to a method similar to that of Example 1, using phosphorus oxychloride, 4-hydroxy-7-fluoro-2,3-dihydrobenzofuran, L-alanine isopropyl ester hydrochloride, pentafluorophenol, and Compound A as starting materials.

The data for structural characterization of the compound are as follows.
ESI-MS: 591.2 (M+1)
$^1$H NMR (DMSO-d$_6$, 400 MHz) δ 7.89 (d, J=8 Hz, 1H), 7.37 (bs, 1H), 7.29 (bs, 1H), 7.10-7.06 (m, 1H), 6.76-6.73 (m, 1H), 6.60-6.54 (m, 1H), 6.15-6.10 (m, 2H), 5.81-5.78 (m, 1H), 5.10-4.90 (m, 2H), 4.72-4.61 (m, 3H), 4.36-4.34 (m, 2H), 4.25-4.20 (m, 1H), 3.78-3.75 (m, 1H), 3.53-3.50 (m, 3H), 3.38-3.35 (m, 2H), 1.23 (d, J=6.4 Hz, 3H), 1.16 (d, J=5.2 Hz, 6H).
$^{31}$P NMR (DMSO-d$_6$, 162 MHz) δ 4.65.

Example 18

(S)-isopropyl 2-(((((2R,3S,4S,5R)-5-(4-amino-2-oxopyrimidin-1(2H)-yl)-4-fluoro-3-hydroxytetrahydrothiophen-2-yl)methoxy)((2,3-dihydrobenzofuran-6-yl)oxy)phosphoryl)amino)propanoate (C18)

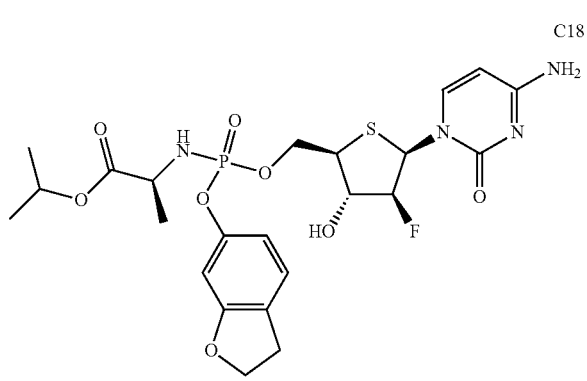

Compound C18 was prepared according to a method similar to that of Example 1, using phosphorus oxychloride, 6-hydroxy-2,3-dihydrobenzofuran, L-alanine isopropyl ester hydrochloride, pentafluorophenol, and Compound A as starting materials.

The data for structural characterization of the compound are as follows.
ESI-MS: 573.2 (M+1)
$^1$H NMR (DMSO-d$_6$, 400 MHz) δ 7.89 (d, J=8 Hz, 1H), 7.35 (bs, 1H), 7.26 (bs, 1H), 7.20-7.18 (m, 1H), 6.68-6.66 (m, 2H), 6.59-6.56 (m, 1H), 6.08-6.03 (m, 1H), 5.80-5.79 (m, 1H), 5.02-4.88 (m, 2H), 4.57 (t, J=8 Hz, 3H), 4.60-4.55 (m, 2H), 4.36-4.32 (m, 1H), 3.80-3.75 (m, 1H), 3.47 (bs, 1H), 3.17-3.13 (m, 2H), 1.23 (d, J=6.4 Hz, 3H), 1.16 (d, J=5.2 Hz, 6H).
$^{31}$P NMR (DMSO-d$_6$, 162 MHz) δ 4.20.

Example 19

(S)-isopropyl 2-(((((2R,3S,4S,5R)-5-(4-amino-2-oxopyrimidin-1(2H)-yl)-4-fluoro-3-hydroxytetrahydrothiophen-2-yl)methoxy)(benzofuran-6-yloxy)phosphoryl)amino)propanoate (C19)

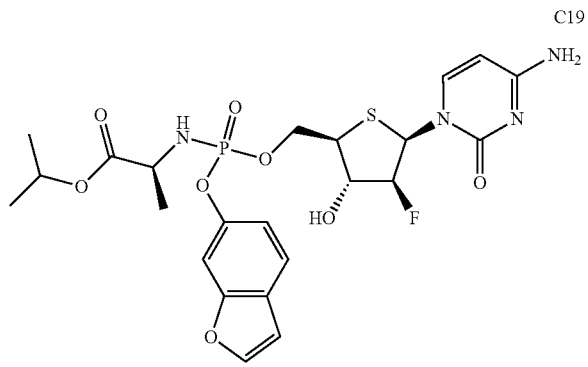 [SMILES: CC(C)OC(=O)[C@H](C)NP(=O)(OC[C@H]1S[C@@H](n2ccc(N)nc2=O)[C@@H](F)[C@@H]1O)Oc1ccc2ccoc2c1]

Compound C19 was prepared according to a method similar to that of Example 1, using phosphorus oxychloride, 6-hydroxy-benzofuran, L-alanine isopropyl ester hydrochloride, pentafluorophenol, and Compound A as starting materials.

The data for structural characterization of the compound are as follows.
ESI-MS: 571.2 (M+1)
$^1$H NMR (DMSO-d$_6$, 400 MHz) δ 7.89 (d, J=8 Hz, 1H), 7.54 (s, 1H), 7.35 (bs, 1H), 7.26 (bs, 1H), 7.20-7.18 (m, 1H), 6.68-6.66 (m, 3H), 6.59-6.56 (m, 1H), 6.08-6.03 (m, 1H), 5.80-5.79 (m, 1H), 5.02-4.88 (m, 2H), 4.60-4.55 (m, 3H), 4.36-4.32 (m, 1H), 3.80-3.75 (m, 1H), 3.47 (bs, 1H), 1.23 (d, J=6.4 Hz, 3H), 1.16 (d, J=5.2 Hz, 6H).
$^{31}$P NMR (DMSO-d$_6$, 162 MHz) δ 4.35.

Biological Assays

Experimental Example 1: In Vitro Experiment

This experimental example was used for the evaluation of the effectiveness of the compounds of the present invention in inhibiting the proliferation of human gastric cancer NCI-N87, colorectal cancer HCT-116, colorectal cancer HCT-15, and pancreatic cancer BxPC-3 cell lines.

1. Cells for the Experiment

The tumor cell lines employed in the present experiment were gastric cancer cell NCI-N87 (obtained from Guangzhou Jennio Biological Technology Co., Ltd.), colorectal cancer cell HCT-116 (obtained from Chengdu Center for Safety Evaluation of Drugs), colorectal cancer cell HCT-15 and pancreatic cancer cell BxPC-3 (both obtained from ATCC, US).

The above cell lines were cultured as a monolayer in vitro, and the culture conditions were as follows. Each of the cell lines is cultured in a corresponding culture medium (RPMI-1640, IMDM and L-15 culture medium (manufacturer: Gibco)) supplemented with 10% heat inactivated Fetal Bovine Serum (manufacturer: Sigma), in an incubator at 37° C. and 5% $CO_2$. The cells were subcultured by treatment with trypsin-EDTA digestion.

2. Sample Preparation

For each type of tumor cells, a blank group, a vehicle group (containing 1‰ DMSO) and 8 groups with a test compound at concentrations of 5 nM, 10 nM, 50 nM, 100 nM, 500 nM, 1000 nM, 5000 nM, and 10000 nM (with each concentration in triplicate) were set.

Appropriate amounts of test compounds were weighted, and dissolved in DMSO (cell culture grade, Sigma) to prepare stock solutions of various concentration gradients according to desired concentrations. During incubation, they were diluted by 1000 times as necessary, and incubation solutions with various drug concentrations were prepared (compound stock solution:medium containing 2% FBS=1:1000).

3. Experimental Method

The experiment was performed according to a CCK-8 method as described below. Cancer cells to be tested were seeded in a 96-well culture plate at a concentration of $5\sim10\times10^4$/mL (100 µL/well), followed by incubation at 37° C. and 5% $CO_2$ for 24 h. The medium was discarded, and incubation solutions with different drug concentrations (200 µL) were respectively added to each well, and the cells were further incubated for 72 h. After the incubation, a CCK-8 solution (20 µL/well) was added to each well to be tested, and the incubation was continued for 4 h in the incubator. OD values at two wavelengths (Detection wavelength: 450 nm, and reference wavelength: 650 nm) were determined on a multifunctional fully-automatic microplate reader.

The inhibitory rate of tumor cell growth was calculated according to the following formula:

Inhibitory rate=$[(OD_{vehicle}-OD_{blank})-(OD_{drug}-OD_{blank})]/(OD_{vehicle}-OD_{blank})*100\%$ Based on the inhibitory rate, a concentration-inhibitory rate curve was fit using GraphPad prism 5.0 software, and $IC_{50}$ was calculated.

FIG. 1 shows that the compound of Example 8 (C8) has potent inhibitory effects on gastric cancer cell NCI-N87, colorectal cancer cell HCT-116, colorectal cancer cell HCT-15, and pancreatic cancer cell BxPC-3 at the above 8 concentrations. $IC_{50}$ values of example compounds of the present invention for each type of cancer cells are shown in table 1-1 to 1-4.

TABLE 1-1

| Compound | $IC_{50}$ (µM) gastric cancer cell NCI-N87 |
| --- | --- |
| C2 | 0.25 |
| C8 | 0.483 |
| C13 | 0.55 |
| C14 | 0.18 |
| C15 | 0.24 |
| C16 | 0.30 |
| C17 | 0.63 |
| C19 | 0.35 |

TABLE 1-2

| Compound | $IC_{50}$ (µM) colorectal cancer cell HCT-116 |
| --- | --- |
| C8 | 0.485 |

TABLE 1-3

| Compound | $IC_{50}$ (µM) colorectal cancer cell HCT-15 |
| --- | --- |
| C2 | 2.97 |
| C8 | 1.964 |
| C14 | 9.78 |
| C15 | 4.08 |

TABLE 1-4

| Compound | $IC_{50}$ (µM) pancreatic cancer cell BxPC-3 |
| --- | --- |
| C2 | 1.28 |
| C8 | 0.705 |
| C14 | 2.82 |
| C15 | 1.80 |
| C16 | 1.15 |
| C17 | 3.80 |
| C18 | 2.74 |
| C19 | 0.68 |

According to the experimental results, the $IC_{50}$ values of the compounds of the present invention were in the range of 0.1-1 µM for gastric cancer cell NCI-N87, in the range of 0.1-1 µM for colorectal cancer cell HCT-116, in the range of 0.5-10 µM for colorectal cancer cell line HCT-15, and in the range of 0.1-5 µM for pancreatic cancer cell BxPC-3. As such, the compounds of the present invention have inhibitory activity on tumor cells.

The compound of Example 8 (C8) of the present invention has a potent anti-tumor effect in vitro, and has excellent inhibitory effects on gastric cancer cell NCI-N87, colorectal cancer cell HCT-116, colorectal cancer cell HCT-15, and pancreatic cancer cell BxPC-3. The compounds of Examples 2, 14 and 15 each have excellent inhibitory effects on gastric cancer cell NCI-N87, colorectal cancer cell HCT-15, and pancreatic cancer cell BxPC-3. The compounds of Examples 16, 17 and 19 have excellent inhibitory effects on gastric cancer cell NCI-N87 and pancreatic cancer cell BxPC-3. The compound of Example 13 has an excellent inhibitory effect on gastric cancer cell NCI-N87, and the compound of Example 18 has an excellent inhibitory effect on pancreatic cancer cell BxPC-3.

Experimental Example 2: In Vivo Activity Test

This experimental example was used for the evaluation of the effectiveness of the compounds of the present invention in inhibiting the proliferation of a subcutaneous xenograft of human tumor cells via various routes of administration.

As an example, the present experimental example investigated variations in tumor volume and body weight of mice with subcutaneous xenografts of human colorectal cancer cell line HCT-116 and gastric cancer cell line NCI-N87 after compound C8 was administered via various routes, so as to determine the pharmacological efficacy and toxicity of each test sample on mice bearing a tumor of colorectal cancer cell HCT-116 or gastric cancer cell NCI-N87.

1. Cell Lines for the Test

Gastric cancer cell NCI-N87 and colorectal cancer cell HCT-116 were cultured as a monolayer in vitro, and the culture conditions were RPMI-1640 culture medium supplemented with 10% heat inactivated Fetal Bovine Serum, and incubation in an incubator at 37° C. and 5% $CO_2$. The cells were subcultured by treatment with trypsin-EDTA digestion.

2. Tumor Cell Inoculation and Grouping of Animals

The tumor cells were respectively inoculated into BALB/c nude mice (SPF grade, female, 16-18 g per mouse, about 6 to 8 weeks old, Beijing Vital River Laboratory Animal Technology Co., Ltd.).

Each nude mouse was inoculated with about $2.5 \times 10^6$ HCT-116 tumor cells or about $3 \times 10^6$ NCI-N87 tumor cells (suspended in 0.1 ml PBS) subcutaneously into the underarm of the right flank. After the inoculated tumor reached a size in the range of about 100-200 mm³, nude mice bearing a tumor that is too small (smaller than 100 mm³) or too big (bigger than 200 mm³) were removed from the study, and the remaining ones were randomized into groups.

3. Sample Preparation

Sulfobutyl ether-β-cyclodextrin (SE-β-CD) was formulated with physiological saline to form a 10% solution, which was then filtered through a 0.22 μm sterile filter for later use.

An appropriate amount of the test compound was weighted, and added in DMSO. The resultant solution was vortexed to uniformity, and the 10% solution of SE-β-CD was added according to the desired concentration. The solution was vortexed to uniformity, and the final concentration of DMSO was adjusted to 5%. A gemcitabine injection (a positive control) was directly diluted to the desired concentration with physiological saline. A 10% solution of SE-β-CD containing 5% DMSO was prepared as a vehicle control.

4. Test Method

Mice bearing a tumor having a volume of about 100-200 mm³ were selected, and randomized into 5 groups (8 mice per group). The dosing volume was 10 mL/kg, and the administration (intravenous administration (i.v.) or oral administration (p.o.)) was performed twice a week for 3 weeks. The tumor volume and body weight were measured twice a week after the administration, and the mortality of animals was observed every day.

5. Test Indexes 5.1 Tumor Volume

The diameter of a tumor was measured, and the tumor volume was calculated according to the following formula: $V = 0.5 \times a \times b^2$, wherein a and b respectively represent the major and minor diameters of a tumor. The anti-tumor effect was evaluated by the tumor growth inhibition (TGI) (%).

$$TGI\ (\%) = [1 - (V_{T-end} - V_{T-start})/(V_{C-end} - V_{C-start})] \times 100\%$$

wherein:

$V_{T-end}$: the mean value of tumor volume of a treatment group at the end of the test;

$V_{T-start}$: the mean value of tumor volume of a treatment group at the beginning of the test;

$V_{C-end}$: the mean value of tumor volume of a vehicle group at the end of the test; and $V_{C-start}$: the mean value of tumor volume of a vehicle group at the beginning of the test.

5.2 Body Weight:

The body weight of an animal was measured twice a week.

6. Test Results 6.1 the Effects on Gastric Cancer Cell NCI-N87

6.1.1 Tumor Regression

Compared with the vehicle control group and the positive control (gemcitabine injection) group, in the groups treated with C8 samples, the tumor growth was significantly inhibited, and various routes of administration of C8 were shown to be safe and well tolerated.

The results of TGI and tumor regression of each group are shown in Table 2.

The results indicated that in the groups treated with C8, complete tumor regression occurred in all the animals, while in the group treated with a gemcitabine injection, complete tumor regression occurred in 2 animals, and partial tumor regression occurred in 6 animals

TABLE 2 the results of TGI and tumor regression in a model of gastric cancer cell NCI-N87.

| Group | Compound | Dosage (μmol/kg) | Administration route | TGI (%) | Tumor regression |
|---|---|---|---|---|---|
| 1 | Vehicle control | — | i.v. | / | 0 |
| 2 | Gemcitabine injection | 190 | i.v. | 107 | 2/8 CR, 6/8 PR |
| 4 | Compound C8 | 190 | i.v. | 109 | 8/8 CR |
| 5 | Compound C8 | 190 | p.o. | 110 | 8/8 CR |

Note:
CR represents complete tumor regression;
PR represents partial tumor regression, i.e., the tumor volume is smaller than that at the beginning of the administration;
i.v. represents intravenous administration; and
p.o. represents oral administration.

6.1.2 Body Weight Change and Mortality of the Animals

At the end of the observation (which was continued for 14 days after the last administration), the body weight of the animals increased in all the groups compared with the weight at the beginning of the administration, and no animal deaths occurred in each group. The results are shown in Table 3.

TABLE 3 body weight change and mortality of the animals in each group

| Group | Compound | Dosage (μmol/kg) | Administration route | Body weight change |
|---|---|---|---|---|
| 1 | Vehicle control | — | i.v. | +11.9% |
| 2 | Gemcitabine injection | 190 | i.v. | +4.8% |
| 4 | Compound C8 | 190 | i.v. | +8.1% |
| 5 | Compound C8 | 190 | p.o. | +8.1% |

On the one hand, in the test on mice bearing a tumor of gastric cancer cell line NCI-N87, compared with the vehicle control group, in the group treated with a gemcitabine injection, complete tumor regression occurred in 2 animals, and partial tumor regression occurred in 6 animals; while complete tumor regression occurred in all the animals from the groups treated with intravenous administration and oral administration of C8, indicating that the tumor growth in animals from groups treated with C8 (i.v. and p.o.) was significantly inhibited.

On the other hand, no animal death occurred in any of the treatment groups. The body weight of the animals increased to different degrees in all the groups, compared with the weight at the beginning of the administration. It was surprisingly found that the percentage body weight increase in the groups treated with compound C8 were twice as much as that in the group treated with a gemcitabine injection. It is shown that the test compound of the present application has significant pharmacological efficacy, as well as better safety and tolerability profiles, and an organism treated with it would recover more easily.

6.2 Colorectal Cancer Cell HCT-116

6.2.1 Tumor Regression

Compared with the vehicle control group and the positive control (gemcitabine injection) group, in the groups treated with compound C8, the tumor growth was significantly inhibited, and compound C8 was shown to have excellent safety and tolerability profiles.

The results of TGI and tumor regression of each group are shown in Table 4.

The results (obtained from observation at 14 days after the last administration) indicated that in the groups treated with compound C8 (i.v. and p.o.), complete tumor regression occurred in 1 animal, and partial tumor regression occurred in 7 animals; while no tumor regression occurred in the group treated with a gemcitabine injection.

TABLE 4 the results of TGI and tumor regression in a model of colorectal cancer cell HCT-116.

| Group | Compound | Dosage (μmol/kg) | Administration route | TGI (%) | Tumor regression |
|---|---|---|---|---|---|
| 1 | Vehicle control | — | i.v. | / | 0 |
| 2 | Gemcitabine injection | 190 | i.v. | 92 | 0 |
| 4 | Compound C8 | 190 | i.v. | 111 | 1/8 CR, 7/8 PR |
| 5 | Compound C8 | 190 | p.o. | 113 | 1/8 CR, 7/8 PR |

6.2.2 Body Weight Change and Mortality of the Animals

At the end of the observation (which was continued for 14 days after the last administration), the body weight of the animals decreased (by 2.4%) in the group treated with a gemcitabine injection, while the body weight of the animals increased in all the remaining groups, compared with the weight at the beginning of the administration. No animal deaths occurred in any of the groups. The detailed results are shown in Table 5.

TABLE 5 body weight change and mortality of the animals in each group

| Group | Compound | Dosage (μmol/kg) | Administration route | Body weight change | Mortality |
|---|---|---|---|---|---|
| 1 | Vehicle control | — | i.v. | +8.6% | 0 |
| 2 | Gemcitabine injection | 190 | i.v. | −2.4% | 0 |
| 4 | Compound C8 | 190 | i.v. | +7.4% | 0 |
| 5 | Compound C8 | 190 | p.o. | +8.9% | 0 |

In the test on mice bearing a tumor of colorectal cancer cell line HCT-116, compared with the vehicle control group, no tumor regression occurred in the group treated with a gemcitabine injection; while in the groups treated with compound C8 (including intravenous administration and oral administration), complete tumor regression occurred in 1 animal, and partial tumor regression occurred in 7 animals. It was thus demonstrated that compound C8 had an excellent anti-tumor effect in vivo. Meanwhile, compound C8 has good polarity and lipid solubility, as well as improved metabolic properties and bioavailability.

Experimental Example 3: In Vivo Activity Test

1. Cell lines for the test, tumor cell inoculation, and grouping of animals

According to methods similar to those in sections 1 to 2 in Experimental example 2, pancreatic cancer cell BxPC-3 was cultured as a monolayer in vitro, and inoculated, and the animals were randomized into groups.

2. Sample Preparation

Sulfobutyl ether-β-cyclodextrin (SE-β-CD) was formulated with physiological saline to form a 10% solution, which was then filtered through a 0.22 μm sterile filter for later use. An appropriate amount of the test compound was weighted out, and added in DMSO. The 10% solution of SE-β-CD was then added according to the desired concentration, and the final concentration of DMSO was adjusted to 2.5%. A gemcitabine injection (a positive control) was diluted to the desired concentration with physiological saline. A 10% solution of SE-β-CD containing 2.5% DMSO was prepared as a vehicle control.

3. Test Method

Mice bearing a tumor having a volume of 100-200 mm$^3$ were selected, and randomized into 14 groups (7 mice per group). The dosing volume was 20 mL/kg, and the administration (intravenous administration (i.v.)) was performed once every 3 days, for 4 times in total. The tumor volume and body weight were measured twice a week after the administration, and the mortality of animals was observed every day.

4. Test Indexes

For statistical calculations of the test indexes, please refer to Experimental example 2.

5. Test Results

TABLE 6 the efficacy on a subcutaneous xenograft of human pancreatic cancer cell BxPC-3 in a nude mouse

| Compound | Dosage (mmol/kg) | Administration route | TGI (%) |
|---|---|---|---|
| Vehicle control | / | i.v. | — |
| Gemcitabine injection | 0.04 | i.v. | −2.2 |
| Compound C8 | 0.04 | i.v. | 26.9 |
| Gemcitabine injection | 0.12 | i.v. | 28.9 |

TABLE 6-continued the efficacy on a subcutaneous xenograft of human
pancreatic cancer cell BxPC-3 in a nude mouse

| Compound | Dosage (mmol/kg) | Administration route | TGI (%) |
|---|---|---|---|
| Compound C8 | 0.12 | i.v. | 74.9 |
| Gemcitabine injection | 0.24 | i.v. | 45.5 |
| Compound C8 | 0.24 | i.v. | 82.9 |

As can be seen from the table above, compound C8 of the present invention can effectively inhibit the growth of a subcutaneous xenograft of human pancreatic cancer cell BxPC-3 in a nude mouse at various dosages, and the pharmacological effect of compound C8 is significantly better than that of the gemcitabine injection.

Experimental Example 4: In Vivo Activity Test

1. Cell Lines for the Test, Tumor Cell Inoculation, Grouping of Animals, and Sample Preparation According to methods similar to those in sections 1 to 3 in Experimental example 2, pancreatic cancer cell BxPC-3 was cultured as a monolayer in vitro, and inoculated; the animals were randomized into groups; and samples were prepared.

2. Test Method

Mice bearing a tumor having a volume of 80-250 mm$^3$ were selected, and randomized into 6 groups (8 mice per group). The dosing volume was 10 mL/kg. The tumor volume and body weight were measured twice a week after the administration, and the mortality of animals was observed every day.

3. Test Indexes

For statistical calculations of the test indexes, please refer to Experimental example 2.

4. Test Results

The test results obtained by administrating twice a week for 3 weeks in total are shown in table 7-1.

TABLE 7-1 the efficacy on a subcutaneous xenograft of human
pancreatic cancer cell BxPC-3 in a nude mouse

| Compound | Dosage (mmol/kg) | Administration route | TGI (%) |
|---|---|---|---|
| Vehicle control | / | p.o. | / |
| Compound C8 | 0.06 | p.o. | 47.7 |
| Gemcitabine injection | 0.12 | i.v. | 23.6 |
| Compound C8 | 0.12 | p.o. | 53.2 |

The test results obtained by administrating (intravenous administration (i.v.) or oral administration (p.o.)) once a week for 3 weeks are shown in table 7-2.

TABLE 7-2 the efficacy on a subcutaneous xenograft of human
pancreatic cancer cell BxPC-3 in a nude mouse

| Compound | Dosage (mmol/kg) | Administration route | TGI (%) |
|---|---|---|---|
| Gemcitabine injection | 0.23 | i.v. | 23.6 |
| Compound C8 | 0.23 | p.o. | 51.0 |

In this test, compound C8 of the present invention can effectively inhibit the growth of a subcutaneous xenograft of human pancreatic cancer cell BxPC-3 in a nude mouse at various dosages, and the pharmacological effect of compound C8 is significantly better than that of the gemcitabine injection. Moreover, compound C8 exhibits excellent oral bioavailability. As oral administration is an administration route more acceptable to a patient, compound C8 of the present invention has improved tolerability in a patient.

Experimental Example 5: In Vivo Activity Test

1. Cell Lines for the Test, Tumor Cell Inoculation, and Grouping of Animals

According to methods similar to those in sections 1 to 2 in Experimental example 2, pancreatic cancer cell Capan-1 was cultured as a monolayer in vitro, and inoculated, and the animals were randomized into groups.

2. Sample Preparation

Samples were prepared as described in Experimental example 2.

3. Test Method

Mice bearing a tumor having a volume of 100-200 mm$^3$ were selected, and randomized into 7 groups (7 mice per group). The dosing volume was 20 mL/kg, and the administration (intravenous administration (i.v.) or oral administration (p.o.)) was performed once every 3 days, for 6 times in total. The tumor volume and body weight were measured twice a week after the administration, and the mortality of animals was observed every day.

4. Test Indexes

For statistical calculations of the test indexes, please refer to Experimental example 2.

5. Test Results

TABLE 8 the efficacy on a subcutaneous xenograft of human
pancreatic cancer cell Capan-1 in a nude mouse

| Compound | Dosage (mmol/kg) | Administration route | TGI (%) |
|---|---|---|---|
| Vehicle control | — | p.o. | — |
| Gemcitabine injection | 0.02 | i.v. | 15.4 |
| Gemcitabine injection | 0.19 | i.v. | 78.9 |
| Compound C8 | 0.02 | p.o. | 25.6 |
| Compound C8 | 0.06 | p.o. | 79.1 |
| Compound C8 | 0.19 | p.o. | 138.5 |
| Compound C8 | 0.06 | i.v. | 81.8 |

As can be seen from the table above, compound C8 of the present invention can effectively inhibit the growth of a subcutaneous xenograft of human pancreatic cancer cell Capan-1 in a nude mouse at various dosages, and the pharmacological effect of compound C8 is significantly better than that of the gemcitabine injection. Moreover, the effects achieved by oral and intravenous administration of compound C8 were better than that achieved by gemcitabine administrated in a dose three times higher than that of C8.

Experimental Example 6: In Vivo Activity Test

This test was performed according to experimental example 5.

Mice bearing a tumor having a volume of 100-200 mm$^3$ were selected, and randomized into 4 groups (6 mice per group). The dosing volume was 10 mL/kg, and the administration (intravenous administration (i.v.) or oral administration (p.o.)) was performed once every 3 days, for 6 times in total. The tumor volume and body weight were measured twice a week after the administration, and the mortality of animals was observed every day.

TABLE 9 the efficacy on a subcutaneous xenograft of human pancreatic cancer cell PANC-1 in a nude mouse

| Compound | Dosage (mmol/kg) | Administration route | TGI (%) |
|---|---|---|---|
| Vehicle control | — | p.o. | — |
| Gemcitabine injection | 0.06 | i.v. | 64.4 |
| Compound C8 | 0.06 | p.o. | 155 |
| Compound C8 | 0.19 | p.o. | 195 |

As can be seen from the table above, compound C8 of the present invention can effectively inhibit the growth of a subcutaneous xenograft of human pancreatic cancer cell Capan-1 in a nude mouse at various dosages, and the pharmacological effect of compound C8 is significantly better than that of the gemcitabine injection.

Experimental Example 7: Toxicology Tests

This experimental example was use to demonstrate the significantly improved safety profile of the compound of present invention.

1. Oral Toxicity Test in Mice (Administration for 7 Days)
Normal Male and female Kunming mice (SPF grade, obtained from Laboratory Animal Center in Sichuan Academy of Chinese Medicine Science) were randomized by weight into groups. The test compound and vehicle control were formulated according to Experimental example 2. The dosage volume was 10 mL/kg, and the administration was performed by oral gavage, once per day for 7 consecutive days.

The mortality and clinical symptoms observed in this test are shown in table 10.

TABLE 10 the results of mortality and clinical symptoms observed in mice administered repeatedly for 7 days

| Group | Sample | Dosage (mg/kg) | Dosage (μmol/kg) | Results (3 Male + 3 Female) |
|---|---|---|---|---|
| 1 | Purified water | 0 | 0 | No abnormal symptoms |
| 2 | Vehicle control | 0 | 0 | No abnormal symptoms |
| 3 | Compound C8 | ~6 | ~12 | No abnormal symptoms |
| 4 | Compound C8 | ~20 | ~38 | No abnormal symptoms |
| 5 | Compound C8 | ~41 | ~77 | One animal arched, and then recovered. |
| 6 | Compound A | ~20 | ~77 | The animals all exhibited severe abnormal symptoms, and two of them died. |

According to the table above, the toxic reactions resulted from about 77 μmol/kg compound A caused the death of some animals, while the death caused by a dosage of about 77 μmol/kg of compound A occurred only when compound C8 was administered at a very high dosage (~115 μmol/kg). Moreover, the animals survived at a dosage of about 77 μmol/kg of compound C8, which indicated that the toxic effects caused by oral administration of this compound to mice were mild, the mice can recover, and the reduced toxicity caused by oral administration of compound C8 to mice was thus demonstrated.

2. Intravenous Toxicity Test in Mice (Administration for 7 Days)

This test was used to investigate the toxic reactions after intravenous administration of compound C8 to normal KM mice for 7 consecutive days.

Test Method

KM mice passing the quarantine control were randomized into 4 groups (3 mice/gender/group). The test compound and vehicle control were formulated according to Experimental example 2. The dosage volume was 10 mL/kg, and the specific dosages were as shown in table 11. The mortality, appearance, behavior, mental status, secretion and excreta etc. of the animals were observed every day for 7 consecutive days after the administration, and the animals were anatomized on day 8.

TABLE 11 dosages

| Group | Drug | Dosage (mg/kg) | Dosage (μmol/kg) | Animal number |
|---|---|---|---|---|
| 1 | Physiological saline | 0 | 0 | 3 male + 3 female |
| 2 | Vehicle control | 0 | 0 | 3 male + 3 female |
| 3 | Compound C8 | 60.9 | 115.38 | 3 male + 3 female |
| 4 | Compound A | 20 | 76.92 | 3 male + 3 female |

Test Results

There was no significant difference of the indexes between the physiological saline group and the vehicle group.

The animals from the group treated with compound A exhibited symptoms such as a hunched stance and weight loss, etc. on day 8, while no relevant abnormalities were observed in group 3 (the group treated with compound C8). The body weight of the animals treated with compound A decreased gradually, and on day 8, the body weight of the female and male mice decreased by 20.2% and 18.1%, respectively; while the body weight of the animals from the group treated with compound C8 increased gradually, and on day 8, the body weight of the female and male mice increased by 13.1% and 26.7%, respectively. Upon anatomy on day 8, compared with the vehicle group, the leukocyte count in the female and male animals from the group treated with compound C8 decreased by 45% and 49%, respectively, and the platelet count decreased by 43% and 39%, respectively; while the leukocyte count in the female and male animals from the group treated with compound A decreased by 83% and 87%, respectively, and the platelet count decreased by 71% and 77%, respectively.

All the compounds in the examples were tested according to the methods described above, and it was found that the compounds in the examples of the present invention have substantially better safety profiles than those of gemcitabine injection and compound A in the toxicology experiments.

By testing the compounds in the examples as described above, it was found that the compounds prepared in the present invention, whether administered intravenously or orally, all achieved excellent anti-tumor effects, and tumors showed complete regression or partial regression. More surprisingly, the pharmacological effects achieved by administering the compounds of the present invention via two different routes were all better than that of the gemcitabine injection (tumors showed no or less regression in the group treated with the gemcitabine injection), and the defect of poor oral bioavailability of gemcitabine was completely overcome.

Unexpectedly, the body weight of the animals in the group treated with the gemcitabine injection decreased during the experiment, indicating that the injection caused certain damages to the test animals; while the body weight of animals in the groups treated with the compounds in the examples of the present invention increased during the experiment, indicating the compounds of the present invention have better tolerability and safety profiles in the animals in different groups.

In summary, the 4'-thio-2'-fluoronucleoside compounds of the present invention have excellent pharmacological effects. Compared with the parent compound (compound A), the compounds of the present invention have increased lipid solubility, improved bioavailability, reduced irritation, improved absorption, and no issues in metabolic rate. The most critical breakthroughs of the compounds of the compounds of the present invention are significantly reduced toxicity, improved safety profile, and efficacy achieved through various routes of administration (intravenous or oral administration).

The present invention has been further described through the above specific embodiments. However, it should not be construed that the scope of the present invention is merely limited to the above examples, technical solutions achieved based on the contents of the present invention all fall within the scope of the present invention.

What is claimed is:

1. A compound, which is:

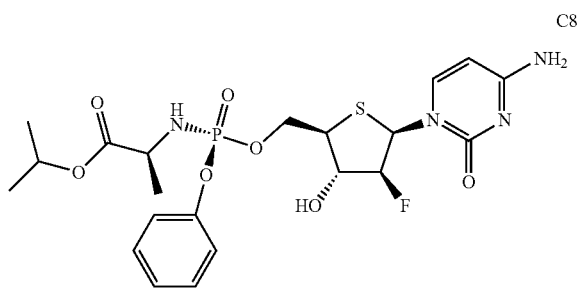

or a pharmaceutically acceptable salt, ester, solvate, hydrate thereof, or racemate thereof, or a mixture thereof.

2. A pharmaceutical composition, comprising the compound according to claim 1, or a pharmaceutically acceptable salt, ester, hydrate, solvate thereof, or racemate thereof, or a mixture thereof, as an active ingredient, and a pharmaceutically acceptable carrier, adjuvant, excipient or equivalent pharmaceutically acceptable medium.

3. The pharmaceutical composition according to claim 2, wherein the pharmaceutical composition comprises the compound in a unit dose ranging from 0.1-1000 mg.

4. The pharmaceutical composition according to claim 3, which is in a form of a solid, semi-solid, liquid, or gas preparation.

5. The pharmaceutical composition according to claim 4, wherein the pharmaceutical composition is in a form of a single dose unit or multiple dose units, each dose unit comprising a suitable amount of the compound, or a pharmaceutically acceptable salt, ester, hydrate, solvate thereof, or racemate thereof, or a mixture thereof.

6. A method for the prevention or treatment of an abnormal cell proliferative disease in a mammal, wherein the method comprises administering to the mammal an effective amount of the compound according to claim 1, or a pharmaceutically acceptable salt, ester, hydrate, solvate thereof, or racemate thereof, or a mixture thereof, wherein the abnormal cell proliferative disease is selected from the group consisting of cancers in esophagus, stomach, intestine, rectum, mouth, pharynx, larynx, lung, colon, breast, uterus, endometrium, ovary, prostate, testis, bladder, kidney, pancreas, bone, connective tissue, skin, eye, brain, and central nervous system, as well as thyroid cancer, leukemia, Hodgkin disease, lymphoma and myeloma.

7. The method according to claim 6, wherein the effective amount of the compound is in a unit dose ranging from 0.1-1000 mg.

8. The method according to claim 7, wherein an additional anti-tumour agent is administered.

9. The method according to claim 8, wherein the effective amount is in a single dose unit or in multiple dose units.

10. The pharmaceutical composition according to claim 3, wherein the pharmaceutical composition comprises the compound in a unit dose ranging from 1-800 mg.

11. The pharmaceutical composition according to claim 10, wherein the pharmaceutical composition comprises the compound in a unit dose ranging from 10-600 mg.

12. The pharmaceutical composition according to claim 11, wherein the pharmaceutical composition comprises the compound in a unit dose ranging from 50-450 mg.

13. The pharmaceutical composition according to claim 12, wherein the pharmaceutical composition comprises the compound in a unit dose ranging from 100-300 mg.

14. The pharmaceutical composition according to claim 4, which is in a dosage form suitable for oral administration.

15. The method according to claim 7, wherein the effective amount of the compound is in a unit dose ranging from 1-800 mg.

16. The method according to claim 15, wherein the effective amount of the compound is in a unit dose ranging from 10-600 mg.

17. The method according to claim 16, wherein the effective amount of the compound is in a unit dose ranging from 50-450 mg.

18. The method according to claim 17, wherein the effective amount of the compound is in a unit dose ranging from 100-300 mg.

* * * * *